US007446185B2

(12) United States Patent
Nelson

(10) Patent No.: US 7,446,185 B2
(45) Date of Patent: Nov. 4, 2008

(54) HER2/NEU TARGET ANTIGEN AND USE OF SAME TO STIMULATE AN IMMUNE RESPONSE

(75) Inventor: Edward L. Nelson, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 505 days.

(21) Appl. No.: 10/484,067

(22) PCT Filed: Jul. 18, 2002

(86) PCT No.: PCT/US02/22975

§ 371 (c)(1),
(2), (4) Date: May 19, 2004

(87) PCT Pub. No.: WO03/055439

PCT Pub. Date: Jul. 10, 2003

(65) Prior Publication Data

US 2004/0241686 A1 Dec. 2, 2004

Related U.S. Application Data

(60) Provisional application No. 60/306,250, filed on Jul. 18, 2001.

(51) Int. Cl.
*C07H 21/04* (2006.01)
*C12N 15/11* (2006.01)
*C12N 15/63* (2006.01)
*C12N 5/10* (2006.01)
*C07K 14/00* (2006.01)

(52) U.S. Cl. .................. 536/23.1; 435/320.1; 435/325; 530/350

(58) Field of Classification Search ................ 536/23.1; 435/320.1, 325; 530/350
See application file for complete search history.

(56) References Cited

U.S. PATENT DOCUMENTS 5,643,576 A 7/1997 Johnston et al.
7,198,920 B1 * 4/2007 Cheever et al. ............ 435/69.7

OTHER PUBLICATIONS

Wei et al. Protection Against Mammary Tumor Growth by Vaccination with Full-Length, Modified Human ErbB-2 DNA International Journal of Cancer 81:748-754, 1999.*
Bargmann and Weinberg (Increased tyrosine kinase activity associated with the protein encoded by the activated neu oncogene, PNAS, 1988 85:5394-5398).*
Bell et al (Rotational Coupling of the Transmembrane and Kinase Domains of the Neu receptor Tyrosine Kinase. Molecular Biology of the Cell, 2000. 11:3589-3599).*
Angelopoulou, K. et al, "p53 Gene Mutation, Tumor p53 Protein Overexpression, and Serum p53 Autoantibody Generation in Patients with Breast Cancer", *Clinical Biochemistry*, vol. 33, No. 1, pp. 53-62, 2000.

Barratt=Bpues. S.M., "Maturation and Trafficking of Monocyte-Derived Dendritic Cells in Monkeys: Implications for Dendritic Cell-Based Vaccines", *The American Association of Immunologists*, vol. 164, pp. 2487-2495, 2000.
Caley, I.J. et al, "Venezuelan equine encephalitis virus vectors expressing HIV-1 proteins: vector design strategies for improved vaccine efficacy", *Vaccine*, vol. 17, pp. 3124-3135, 1999.
Davis, N.L. et al, "A Viral Vaccine Vector That Expresses Foreign Genes in Lymph Nodes and Protects against Mucosal Challenge", *Journal of Virology*, vol. 70, No. 6, pp. 3781-3787, 1996.
Disis, M.L. et al., "Generation of Immunity to the HER-2/*neu* Oncogenic Protein in Patients with Breast and Ovarian Cancer Using a Peptide-based Vaccine", *Clinical Cancer Research*, vol. 5, pp. 1289-1297, 1999.
Disis, M.L, et al, "Delayed-Type Hypersensitivityy Response Is a Predictor of Peripheral Blood T-Cell Immunity after HER-2/neu Peptide Immunization", *Clinical Cancer Research*, vol. 6, pp. 1347-1350, 2000.
Fong, L. Engleman, Ed., "Dendritic Cells in Cancer Immunotherapy", *Annu. Rev. Immunol.*, vol. 18, pp. 245-273, 2000.
Hevey, M. et al., "Marburg Virus Vaccines Based upon Alphavirus Replicons Protect Guinea Pigs and Nonhuman Primates", *Virology*, vol. 251, pp. 28-37, 1998.
MacDonald, G. and Johnson, R., "Role of Dendritic Cell Targeting in Venezuelan Equine Encephalitis Virus Pathogenesis", *Journal of Virology*, vol. 74, No. 2, pp. 914-922, 2000.
Marincola, F. M. et al, "Escape of Human Solid Tumors from T-Cell Recognition: Molecular Mechanisms and Functional Significance", *Advances in Immunology*, vol. 74, pp. 181-273, 2000.
Montoya, M. and del Val, M., "Intracellular Rate-Limiting Steps in MHC Class I Antigen Processing", *The American Association of Immunologists*, vol. 163, pp. 1914-1922, 1999.
Morse, M.A., et al, "Migration of Human Dendritic Cells after Injection in Patients with Metastatic Malignancies", *Cancer Research*, vol. 59, pp. 56-58, 1999.
Riker, A. et al., "Immune selection after antigen-specific immunotherapy of melanoma", *Surgery*, vol. 126, No. 2, pp. 112-120, 1999.
Sandmaier, B.M. et al., "Evidence of a Cellular Immune Response Against Sialyl-Tn in Breast and Ovarian Cancer Patients After High-Dose Chemotherapy, Stem Cell Rescue, and immunization with Theratope STn-KLH Cancer Vaccine", *Journal of Immunotherapy*, vol. 22, pp. 54-66, 1999.
Slinghuff, Jr., C.L. et al., "Melanomas with concordant loss of multiple melanocytic differentiation proteins: immune escape that may be overcome by targeting unique or undefined antigens", *Cancer Immunol Immunother*, vol. 48, pp. 661-672, 2000.
Tuttle, T.M. et al., "Proliferative and Cytokine Responses to Class II HER-2/neu-associated Peptides in Breast Cancer Patients", *Clinical Cancer Research*, vol. 4, pp. 2015-2024, 1998.

(Continued)

*Primary Examiner*—Anne Marie S Wehbe
(74) *Attorney, Agent, or Firm*—DLA Piper LLP (US)

(57) ABSTRACT

A recombinant polynucleotide encoding a Her2/neu target antigen is provided, as is a recombinant Her2/neu target antigen polypeptide. Also provided are methods of using such a recombinant polynucleotide to express a Her2/neu target antigen in a cell. In addition, methods are provided for using the recombinant polynucleotide or the recombinant polypeptide to stimulate an immune response in a subject against cancer that expresses Her2/neu. Methods of making a target antigen also are provided.

23 Claims, 12 Drawing Sheets

OTHER PUBLICATIONS

Vitale, M. et al., "HLA Class I Antigen and Transporter Associated with Antigen Processing (TAP1 and TAP2) Down-Regulation in High-Grade Primary Breast Carcinoma Lesions", *Cancer Research*, vol. 58, pp. 737-742, 1998.

Yewdell, J.W., et al., "Mechanisms of Exogenous Antigen Presentation by MHC Class I Molecules in Vivo: Implications for Generating CD8+ T Cell Responses to Infectious Agents, Tumors, Transplants, and Vaccines", *Advances in Immunology*, vol. 73, pp. 1-77, 1999.

GenBank 017003 Houliston, R.S. et al., "Characterization of the proto-oncogenic and mutant forms of the transmembrane region of Neu in micelles", *J. Biol. Chem.*, vol. 79, No. 23, pp. 24073-24080, 2004.

Entrez P06494 Bargmann, C.I. et al., "The neu oncogene encodes an epidermal growth factor receptor-related protein", *Nature*, vol. 319, pp. 226-230, 1986.

Entrez P04626 Yamamoto, T. et al., "Similarity of protein encoded by the human c-erb-B-2 gene to epidermal growth factor receptor", *Nature*, vol. 319, pp. 230-234, 1986.

GenBank 004448 Ueda, Y. et al., "HER2 signaling enhances 5'UTR-mediated translation of c-Myc mRNA", *J. Biol. Chem.*, vol. 279, No. 23, pp. 24505-24513, 2004.

\* cited by examiner

FIGURE 1A

```
h   MELAALCRWGLLLALLPPGAASTQVCTGTDMKLRLPASPETHLDMLRHLYQGCQ
r       W    F           I G

VVQGNLELTYLPTNASLSFLQDIQEVQGYVLIAHNQVRQVPLQRLRIVRGTQLFEDN
            V A                  M       KR                K

YALAVLDNGDPLNNTTPVTGASPG GLRELQLRSLTEILKGGVLIQRNPQLCYQDTIL
             R    QD VAAS PGRTPE                  RG      MV

WKDIFHKNNQLALTLIDTNRSRACHPCSPMCKGSRCWGESSEDCQSLTRTVCAGGC
         V R      PVD        P  A A   DNH         I G I  TS

ARCKGPLPTDCCHEQCAAGCTGPKHSDCLACLHFNHSGICELHCPALVTYNTDTFES
       R

MPNPEGRYTFGASCVTACPYNYLSTDVGSCTLVCPLHNQEVTAEDGTQRCEKCSKP
       H               T         E      PN

CARVCYGLGMEHLREVRAVTSANIQEFAGCKKIFGSLAFLPESFDGDPASNTAPLQP
                    GA   I  D V  D                 S GI    R

EQLQVFETLEEITGYLYISAWPDSLPDLSVFQNLQVIRGRILHNGAYSLTLQGLGISWL
                                          RI    D            HS

GLRSLRELGSGLALIHHNTHLCFVHTVPWDQLFRNPHQALLHTANRPEDE CVGEGL
              R A                                 SG      EDLCVSS

ACHQLCARGHCWGPGPTQCVNCSQFLRGQECVEECRVLQGLPREYVNARHCLPCH
     V NS    H              H              WK        SDKR

PECQPQNGSVTCFGPEADQCVACAHYKDPPFCVARCPSGVKPDLSYMPIWKFPDEE
           S E   S      A       SSS                    Y

GACQPCPINCTHSCVDLDDKGCPAEQRASPLTSIISAVVGILLVVVLGVVFGILIKRR
             I            ER        V F AT  GV  FLI V V       .

QQKIRKYTMRRLLQETELVEPLTPSGAMPNQAQMRILKETELRKVKVLGSGAFGTV
    R
```

FIGURE 1B

YKGIWIPDGENVKIPVAIKVLRENTSPKANKEILDEAYVMAGVGSPYVSRLLGICLTS

TVQLVTQLMPYGCLLDHVRENRGRLGSQDLLNWCMQIAKGMSYLEDVRLVHRDL
           H                              V

AARNVLVKSPNHVKITDFGLARLLDIDETEYHADGGKVPIKWMALESILRRRFTHQS

DVWSYGVTVWELMTFGAKPYDGIPAREIPDLLEKGERLPQPPICTIDVYMIMVKCW

MIDSECRPRFRELVSEFSRMARDPQRFVVIQNEDLGPASPLDSTFYRSLLEDDDMGD
                                        S   M

LVDAEEYLVPQQGFFCPD<u>PAPGAGGMVHHRHRSSSTRSGGGDLTLGLEPSEEEAPRS</u>
                    S   T    T  ST    R          E          GP

<u>PLAPSEGAGSDVFDGDLGMGAAKGLQSLPTHDPSPLQRYSEDPTVPLPSETDGYVAP</u>
         A    VT    SP  L      L    P

<u>LTCSPQPEYVNQPDVRPQPPSPREGPLPAARPAGATLERPKTLSPGKNGVVKDVFAF</u>
 A      SE Q Q    LTP      PV

<u>GGAVENPEYLTPQGGAAPQPHPPPAFSPAFDNLYYWDQDPPERGAPPSTFKGTPTAE</u>
    V RE  T SP   S              NSS Q P    NE

<u>NPEYLGLDVPV</u>

Time (days post-tumor re-challenge)

FIGURE 6A

RAT Her2/NEU TARGET ANTIGEN SEQUENCE

<u>ATGGCC</u>TCCTGTGTGGATCTGGATGAACGAGGCTGCCCAGCAGAGCAGAGAGCC
AGCCCGGTGACATTCATCATTGCAACTGTAGTGGGCGTCCTGCTGTTCCTGATCTT
AGTGGTGGTCGTTGGAATCCTAATCAAACGAAGGAGACAGAAG<u>ATCCGG</u>AGCCC
TACCCCAGGCACTGGGAGCACAGCCCATAGAAGGCACCGCAGCTCGTCCACCAG
GAGTGGAGGTGGTGAGCTGACACTGGGCCTGGAGCCCTCGGAAGAAGGGCCCCC
CAGATCTCCACTGGCTCCCTCGGAAGGGGCTGGCTCCGATGTGTTTGATGGTGAC
CTGGCAATGGGGGTAACCAAAGGGCTGCAGAGCCTCTCTCCACATGACCTCAGC
CCTCTACAGCGGTACAGCGAGGACCCCACATTACCTCTGCCCCCCGAGACTGATG
GCTATGTTGCTCCCCTGGCCTGCAGCCCCAGCCCGAGTATGTGAACCAATCAGA
GGTTCAGCCTCAGCCTCCTTTAACCCCAGAGGGTCCTCTGCCTCCTGTCCGGCCTG
CTGGTGCTACTCTAGAAAGACCCAAGACTCTCTCCTGGGAAGAATGGGGTTGT
CAAAGACGTTTTTGCCTTCGGGGGTGCTGTGGAGAACCCTGAATACTTAGTACCG
AGAGAAGGCACTGCCTCTCCGCCCCACCCTTCTCCTGCCTTCAGCCCAGCCTTTG
ACAACCTCTATTACTGGGACCAGAACTCATCGGAGCAGGGGCCTCCACCAAGTA
ACTTTGAAGGGACCCCCACTGCAGAGAACCCTGAGTACCTAGGCCTGGATGTAC
CTGTATGA (SEQ ID NO:3)

RAT Her2/NEU TARGET ANTIGEN PROTEIN SEQUENCE

<u>MA</u>SCVDLDERGCPAEQRASPVTFIIATVVGVLLFLILVVVVGILKRRRQK<u>IRS</u>PTPGT
GSTAHRRHRSSSTRSGGGELTLGLEPSEEGPPRSPLAPSEGAGSDVFDGDLAMGVTK
GLQSLSPHDLSPLQRYSEDPTLPLPPETDGYVAPLACSPQPEYVNQSEVQPQPPLTPEG
PLPPVRPAGATLERPKTLSPGKNGVVKDVFAFGGAVENPEYLVPREGTASPPHPSPAF
SPAFDNLYYWDQNSSEQGPPPSNFEGTPTAENPEYLGLDVPV (SEQ ID NO:4)

Proximal rat Her2/neu polypeptide scvdldergcpaeqraspvtfiiatvvgvllflilvvvvgilikrrrqkir (SEQ ID NO:5)

Proximal rat Her2/neu nucleotide tcctgtgtggatctggatgaacgaggctgcccagcagagcagagagccagcccggtgacattcatcattgcaactgtagagggcgtc
ctgctgttcctgatcttagtggtggtcgttggaatcctaatcaaacgaaggagacagaaga<u>tccgg(a)</u> (SEQ ID NO:6)

FIGURE 6B

Terminal rat Her2/neu polypeptide ptpgtgstahrrhrssstrsgggeltlglepseegpprsplapsegagsdvfdgdlamgvtkglqslsphdlsplqrysedptlplppe
tdgyvaplacspqpeyvnqsevqpqppltpegplppvrpagatlerpktlspgkngvvkdvfafggavenpeylvpregtaspp
hpspafspafdnlyywdqnsseqgpppsnfegtptaenpeylgldvpv (SEQ ID NO:7)

Terminal Her2/rat neu nucleotide

<u>tccgga</u>Gccctaccccaggcactgggagcacagcccatagaaggcaccgcagctcgtccaccaggagtggaggtggtgagctga
cactgggcctggagccctcggaagaagggcccccagatctccactggctccctcggaagggggctggctccgatgtgtttgatggtg
acctggcaatgggggtaaccaaagggctgcagagcctctctccacatgacctcagccctctacagcggtacagcgaggacccaca
ttacctctgcccccgagactgatggctatgttgctcccctggcctgcagccccagcccgagtatgtgaaccaatcagaggttcagcc
tcagcctcctttaaccccagagggtcctctgcctcctgtccggcctgctggtgctactctagaaagacccaagactctctctcctgggaa
gaatggggttgtcaaagacgtttttgccttcggggtgctgtggagaacccctgaatacttagtaccgagagaaggcactgcctctccgc
cccacccttctcctgccttcagcccagcctttgacaacctctattactgggaccagaactcatcggagcaggggcctccaccaagtaac
tttgaagggacccccactgcagagaaccctgagtacctaggcctggatgtacctgtatga (SEQ ID NO:8)

FIGURES 7A

HUMAN Her2/neu nucleotide sequence

<u>atggcc</u>tgtgtggacctggatgacaagggctgccccgccgagcagagagccagccctctgacgtccatcgtctctgcggtggttggc
attctgctggtcgtggtcttgggggtggtctttgggatcctcatcaagcgacggcagcagaaga<u>tccggagccctg</u>ccccgggcgctg
ggggcatggtccaccacaggcaccgcagctcatctaccaggagtggcggtggggacctgacactagggctggagccctctgaaga
ggaggcccccaggtctccactggcaccctccgaaggggctggctccgatgtatttgatggtgacctgggaatgggggcagccaagg
ggctgcaaagcctccccacacatgacccagccctctacagcggtacagtgaggaccccacagtaccctgcctctgagactgatg
gctacgttgccccctgacctgcagccccagcctgaatatgtgaaccagccagatgttcggccccagccccttcgccccgagagg
gccctctgcctgctgcccgacctgctggtgccactctggaaagggccaagactctctccccagggaagaatggggtcgtcaaagacg
ttttgcctttggggggtgccgtggagaaccccgagtacttgacaccccagggaggagctgcccctcagcccaccctcctcctgccttc
agcccagccttcgacaacctctattactgggaccaggacccaccagagcggggggctccacccagcaccttcaaagggacacctac
ggcagagaacccagagtacctgggtctggacgtgccagtgtga (SEQ ID NO:9)

HUMAN Her2/neu polypeptide Target Antigen

<u>MA</u>CVDLDDKGCPAEQRASPLTSIVSAVVGILLVVVLGVVFGILIKRRQQK<u>IRSP</u>APGA
GGMVHHRHRSSSTRSGGGDLTLGLEPSEEEAPRSPLAPSEGAGSDVFDGDLGMGAA
KGLQSLPTHDPSPLQRYSEDPTVPLPSETDGYVAPLTCSPQPEYVNQPDVRPQPPSPRE
GPLPAARPAGATLERAKTLSPGKNGVVKDVFAFGGAVENPEYLTPQGGAAPQPHPPP
AFSPAFDNLYYWDQDPPERGAPPSTFKGTPTAENPEYLGLDVPVZ (SEQ ID NO:10)

Proximal human Her 2/neu polypeptide cvdlddkgcpaeqraspltsiisavvgillvvvlgvvfgilikrrqqkir (SEQ ID NO:11)

Proximal human Her 2/neu nucleotide

Tgtgtggacctggatgacaagggctgccccgccgagcagagagccagccctctgacgtccatcgtctctgcggtggttggcattctg
ctggtcgtggtcttgggggtggtctttgggatcctcatcaagcgacggcagcagaaga<u>tccgga</u> (SEQ ID NO:12)

FIGURE 7B

Distal human Her 2/neu polypeptide cpdpapgaggmvhhrhrssstrsgggdltlglepseeeaprsplapsegagsdvfdgdlgmgaakglqslpthdpsplqrysedp
tvplpsetdgyvapltcspqpeyvnqpdvrpqppspregplpaarpagatlerpktlspgkngvvkdvfafggavenpeyltpqg
gaapqphpppafspafdnlyywdqdppergappstfkgtptaenpeylgldvpv  (SEQ ID NO:13)

Distal human Her 2/neu nucleotide

<u>ttctgtcc(a/g)gaG</u>ccctgccccgggcgctgggggcatggtccaccacaggcaccgcagctcatctaccaggagtggcggtggg
gacctgacactagggctggagccctctgaagaggaggcccccaggtctccactggcaccctccgaaggggctggctccgatgtattt
gatggtgacctgggaatgggggcagccaaggggctgcaaagcctccccacacatgaccccagccctctacagcggtacagtgagg
accccacagtacccctgccctctgagactgatggctacgttgcccccctgacctgcagccccagcctgaatatgtgaaccagccaga
tgttcggccccagcccccttcgccccgagagggccctctgcctgctgcccgacctgctggtgccactctggaagggccaagactct
ctcccagggaagaatggggtcgtcaaagacgtttttgcctttggggtgccgtggagaaccccgagtacttgacacccaggggagg
agctgccctcagccccaccctcctcctgccttcagcccagccttcgacaacctctattactgggaccaggacccaccagagcgggg
ggctccacccagcaccttcaaagggacacctacggcagagaacccagagtacctgggtctggacgtgccagtgtga  (SEQ ID NO:14)

SEQUENCE LISTING

<160> NUMBER OF SEQ ID NOS: 14

<210> SEQ ID NO 1
<211> LENGTH: 1255
<212> TYPE: PRT
<213> ORGANISM: Homo sapiens

<400> SEQUENCE: 1

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

```
Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
            130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
            210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
            515                 520                 525
```

```
Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
930                 935                 940

Pro Ile Cys Thr Ile Asp Val Tyr Met Ile Met Val Lys Cys Trp Met
```

-continued

```
            945                 950                 955                 960
    Ile Asp Ser Glu Cys Arg Pro Arg Phe Arg Glu Leu Val Ser Glu Phe
                    965                 970                 975
    Ser Arg Met Ala Arg Asp Pro Gln Arg Phe Val Val Ile Gln Asn Glu
                    980                 985                 990
    Asp Leu Gly Pro Ala Ser Pro Leu Asp Ser Thr Phe Tyr Arg Ser Leu
                    995                 1000                1005
    Leu Glu Asp Asp Met Gly Asp Leu Val Asp Ala Glu Glu Tyr
            1010                1015                1020
    Leu Val Pro Gln Gln Gly Phe Phe Cys Pro Asp Pro Ala Pro Gly
            1025                1030                1035
    Ala Gly Gly Met Val His His Arg His Arg Ser Ser Thr Arg
            1040                1045                1050
    Ser Gly Gly Gly Asp Leu Thr Leu Gly Leu Glu Pro Ser Glu Glu
            1055                1060                1065
    Glu Ala Pro Arg Ser Pro Leu Ala Pro Ser Glu Gly Ala Gly Ser
            1070                1075                1080
    Asp Val Phe Asp Gly Asp Leu Gly Met Gly Ala Ala Lys Gly Leu
            1085                1090                1095
    Gln Ser Leu Pro Thr His Asp Pro Ser Pro Leu Gln Arg Tyr Ser
            1100                1105                1110
    Glu Asp Pro Thr Val Pro Leu Pro Ser Glu Thr Asp Gly Tyr Val
            1115                1120                1125
    Ala Pro Leu Thr Cys Ser Pro Gln Pro Glu Tyr Val Asn Gln Pro
            1130                1135                1140
    Asp Val Arg Pro Gln Pro Pro Ser Pro Arg Glu Gly Pro Leu Pro
            1145                1150                1155
    Ala Ala Arg Pro Ala Gly Ala Thr Leu Glu Arg Pro Lys Thr Leu
            1160                1165                1170
    Ser Pro Gly Lys Asn Gly Val Val Lys Asp Val Phe Ala Phe Gly
            1175                1180                1185
    Gly Ala Val Glu Asn Pro Glu Tyr Leu Thr Pro Gln Gly Gly Ala
            1190                1195                1200
    Ala Pro Gln Pro His Pro Pro Ala Phe Ser Pro Ala Phe Asp
            1205                1210                1215
    Asn Leu Tyr Tyr Trp Asp Gln Asp Pro Pro Glu Arg Gly Ala Pro
            1220                1225                1230
    Pro Ser Thr Phe Lys Gly Thr Pro Thr Ala Glu Asn Pro Glu Tyr
            1235                1240                1245
    Leu Gly Leu Asp Val Pro Val
            1250                1255

<210> SEQ ID NO 2
<211> LENGTH: 1257
<212> TYPE: PRT
<213> ORGANISM: Rattus norvegicus

<400> SEQUENCE: 2

Met Glu Leu Ala Ala Trp Cys Arg Trp Gly Phe Leu Leu Ala Leu Leu
1               5                   10                  15
Pro Pro Gly Ile Ala Gly Thr Gln Val Cys Thr Gly Thr Asp Met Lys
                20                  25                  30
Leu Arg Leu Pro Ala Ser Pro Glu Thr His Leu Asp Met Leu Arg His
        35                  40                  45
```

```
Leu Tyr Gln Gly Cys Gln Val Val Gln Gly Asn Leu Glu Leu Thr Tyr
     50                  55                  60
Val Pro Ala Asn Ala Ser Leu Ser Phe Leu Gln Asp Ile Gln Glu Val
 65                  70                  75                  80
Gln Gly Tyr Met Leu Ile Ala His Asn Gln Val Lys Arg Val Pro Leu
                 85                  90                  95
Gln Arg Leu Arg Ile Val Arg Gly Thr Gln Leu Phe Glu Asp Lys Tyr
            100                 105                 110
Ala Leu Ala Val Leu Asp Asn Arg Asp Pro Gln Asp Asn Val Ala Ala
            115                 120                 125
Ser Thr Pro Gly Arg Thr Pro Glu Gly Leu Arg Glu Leu Gln Leu Arg
    130                 135                 140
Ser Leu Thr Glu Ile Leu Lys Gly Gly Val Leu Ile Arg Gly Asn Pro
145                 150                 155                 160
Gln Leu Cys Tyr Gln Asp Met Val Leu Trp Lys Asp Val Phe Arg Lys
                165                 170                 175
Asn Asn Gln Leu Ala Pro Val Asp Ile Asp Thr Asn Arg Ser Arg Ala
                180                 185                 190
Cys Pro Pro Cys Ala Pro Ala Cys Lys Asp Asn His Cys Trp Gly Glu
        195                 200                 205
Ser Pro Glu Asp Cys Gln Ile Leu Thr Gly Thr Ile Cys Thr Ser Gly
    210                 215                 220
Cys Ala Arg Cys Lys Gly Arg Leu Pro Thr Asp Cys Cys His Glu Gln
225                 230                 235                 240
Cys Ala Ala Gly Cys Thr Gly Pro Lys His Ser Asp Cys Leu Ala Cys
                245                 250                 255
Leu His Phe Asn His Ser Gly Ile Cys Glu Leu His Cys Pro Ala Leu
                260                 265                 270
Val Thr Tyr Asn Thr Asp Thr Phe Glu Ser Met His Asn Pro Glu Gly
            275                 280                 285
Arg Tyr Thr Phe Gly Ala Ser Cys Val Thr Thr Cys Pro Tyr Asn Tyr
    290                 295                 300
Leu Ser Thr Glu Val Gly Ser Cys Thr Leu Val Cys Pro Pro Asn Asn
305                 310                 315                 320
Gln Glu Val Thr Ala Glu Asp Gly Thr Gln Arg Cys Glu Lys Cys Ser
                325                 330                 335
Lys Pro Cys Ala Arg Val Cys Tyr Gly Leu Gly Met Glu His Leu Arg
            340                 345                 350
Gly Ala Arg Ala Ile Thr Ser Asp Asn Val Gln Glu Phe Asp Gly Cys
        355                 360                 365
Lys Lys Ile Phe Gly Ser Leu Ala Phe Leu Pro Glu Ser Phe Asp Gly
    370                 375                 380
Asp Pro Ser Ser Gly Ile Ala Pro Leu Arg Pro Glu Gln Leu Gln Val
385                 390                 395                 400
Phe Glu Thr Leu Glu Glu Ile Thr Gly Tyr Leu Tyr Ile Ser Ala Trp
                405                 410                 415
Pro Asp Ser Leu Arg Asp Leu Ser Val Phe Gln Asn Leu Arg Ile Ile
            420                 425                 430
Arg Gly Arg Ile Leu His Asp Gly Ala Tyr Ser Leu Thr Leu Gln Gly
        435                 440                 445
Leu Gly Ile His Ser Leu Gly Leu Arg Ser Leu Arg Glu Leu Gly Ser
    450                 455                 460
Gly Leu Ala Leu Ile His Arg Asn Ala His Leu Cys Phe Val His Thr
```

```
           465                 470                 475                 480
Val Pro Trp Asp Gln Leu Phe Arg Asn Pro His Gln Ala Leu Leu His
                485                 490                 495

Ser Gly Asn Arg Pro Glu Glu Asp Leu Cys Val Ser Ser Gly Leu Val
                500                 505                 510

Cys Asn Ser Leu Cys Ala His Gly His Cys Trp Gly Pro Gly Pro Thr
                515                 520                 525

Gln Cys Val Asn Cys Ser His Phe Leu Arg Gly Gln Glu Cys Val Glu
            530                 535                 540

Glu Cys Arg Val Trp Lys Gly Leu Pro Arg Glu Tyr Val Ser Asp Lys
545                 550                 555                 560

Arg Cys Leu Pro Cys His Pro Glu Cys Gln Pro Gln Asn Ser Ser Glu
                565                 570                 575

Thr Cys Phe Gly Ser Glu Ala Asp Gln Cys Ala Ala Cys Ala His Tyr
                580                 585                 590

Lys Asp Ser Ser Ser Cys Val Ala Arg Cys Pro Ser Gly Val Lys Pro
            595                 600                 605

Asp Leu Ser Tyr Met Pro Ile Trp Lys Tyr Pro Asp Glu Glu Gly Ile
            610                 615                 620

Cys Gln Pro Cys Pro Ile Asn Cys Thr His Ser Cys Val Asp Leu Asp
625                 630                 635                 640

Glu Arg Gly Cys Pro Ala Glu Gln Arg Ala Ser Pro Val Thr Phe Ile
                645                 650                 655

Ile Ala Thr Val Val Gly Val Leu Leu Phe Leu Ile Leu Val Val Val
                660                 665                 670

Val Gly Ile Leu Ile Lys Arg Arg Gln Lys Ile Arg Lys Tyr Thr
            675                 680                 685

Met Arg Arg Leu Leu Gln Glu Thr Glu Leu Val Glu Pro Leu Thr Pro
            690                 695                 700

Ser Gly Ala Met Pro Asn Gln Ala Gln Met Arg Ile Leu Lys Glu Thr
705                 710                 715                 720

Glu Leu Arg Lys Val Lys Val Leu Gly Ser Gly Ala Phe Gly Thr Val
                725                 730                 735

Tyr Lys Gly Ile Trp Ile Pro Asp Gly Glu Asn Val Lys Ile Pro Val
            740                 745                 750

Ala Ile Lys Val Leu Arg Glu Asn Thr Ser Pro Lys Ala Asn Lys Glu
            755                 760                 765

Ile Leu Asp Glu Ala Tyr Val Met Ala Gly Val Gly Ser Pro Tyr Val
            770                 775                 780

Ser Arg Leu Leu Gly Ile Cys Leu Thr Ser Thr Val Gln Leu Val Thr
785                 790                 795                 800

Gln Leu Met Pro Tyr Gly Cys Leu Leu Asp His Val Arg Glu His Arg
                805                 810                 815

Gly Arg Leu Gly Ser Gln Asp Leu Leu Asn Trp Cys Val Gln Ile Ala
                820                 825                 830

Lys Gly Met Ser Tyr Leu Glu Asp Val Arg Leu Val His Arg Asp Leu
            835                 840                 845

Ala Ala Arg Asn Val Leu Val Lys Ser Pro Asn His Val Lys Ile Thr
850                 855                 860

Asp Phe Gly Leu Ala Arg Leu Leu Asp Ile Asp Glu Thr Glu Tyr His
865                 870                 875                 880

Ala Asp Gly Gly Lys Val Pro Ile Lys Trp Met Ala Leu Glu Ser Ile
                885                 890                 895
```

```
Leu Arg Arg Arg Phe Thr His Gln Ser Asp Val Trp Ser Tyr Gly Val
            900                 905                 910

Thr Val Trp Glu Leu Met Thr Phe Gly Ala Lys Pro Tyr Asp Gly Ile
        915                 920                 925

Pro Ala Arg Glu Ile Pro Asp Leu Leu Glu Lys Gly Glu Arg Leu Pro
        930                 935                 940

Gln Pro Pro Ile Cys Thr Ile Asp Val Tyr Met Ile Met Val Lys Cys
945                 950                 955                 960

Trp Met Ile Asp Ser Glu Cys Arg Pro Arg Phe Arg Glu Leu Val Ser
                965                 970                 975

Glu Phe Ser Arg Met Ala Arg Asp Pro Gln Arg Phe Val Val Ile Gln
            980                 985                 990

Asn Glu Asp Leu Gly Pro Ser Ser Pro Met Asp Ser Thr Phe Tyr Arg
            995                 1000                1005

Ser Leu Leu Glu Asp Asp Asp Met Gly Asp Leu Val Asp Ala Glu
    1010                1015                1020

Glu Tyr Leu Val Pro Gln Gln Gly Phe Phe Ser Pro Asp Pro Thr
    1025                1030                1035

Pro Gly Thr Gly Ser Thr Ala His Arg Arg His Arg Ser Ser Ser
    1040                1045                1050

Thr Arg Ser Gly Gly Gly Glu Leu Thr Leu Gly Leu Glu Pro Ser
    1055                1060                1065

Glu Glu Gly Pro Pro Arg Ser Pro Leu Ala Pro Ser Glu Gly Ala
    1070                1075                1080

Gly Ser Asp Val Phe Asp Gly Asp Leu Ala Met Gly Val Thr Lys
    1085                1090                1095

Gly Leu Gln Ser Leu Ser Pro His Asp Leu Ser Pro Leu Gln Arg
    1100                1105                1110

Tyr Ser Glu Asp Pro Thr Leu Pro Leu Pro Pro Glu Thr Asp Gly
    1115                1120                1125

Tyr Val Ala Pro Leu Ala Cys Ser Pro Gln Pro Glu Tyr Val Asn
    1130                1135                1140

Gln Ser Glu Val Gln Pro Gln Pro Pro Leu Thr Pro Glu Gly Pro
    1145                1150                1155

Leu Pro Pro Val Arg Pro Ala Gly Ala Thr Leu Glu Arg Pro Lys
    1160                1165                1170

Thr Leu Ser Pro Gly Lys Asn Gly Val Val Lys Asp Val Phe Ala
    1175                1180                1185

Phe Gly Gly Ala Val Glu Asn Pro Glu Tyr Leu Val Pro Arg Glu
    1190                1195                1200

Gly Thr Ala Ser Pro Pro His Pro Ser Pro Ala Phe Ser Pro Ala
    1205                1210                1215

Phe Asp Asn Leu Tyr Tyr Trp Asp Gln Asn Ser Ser Glu Gln Gly
    1220                1225                1230

Pro Pro Pro Ser Asn Phe Glu Gly Thr Pro Thr Ala Glu Asn Pro
    1235                1240                1245

Glu Tyr Leu Gly Leu Asp Val Pro Val
    1250                1255

<210> SEQ ID NO 3
<211> LENGTH: 828
<212> TYPE: DNA
<213> ORGANISM: Rat
```

<400> SEQUENCE: 3

```
atggcctcct gtgtggatct ggatgaacga ggctgcccag cagagcagag agccagcccg      60
gtgacattca tcattgcaac tgtagtgggc gtcctgctgt tcctgatctt agtggtggtc     120
gttggaatcc taatcaaacg aaggagacag aagatccgga gccctacccc aggcactggg     180
agcacagccc atagaaggca ccgcagctcg tccaccagga gtggaggtgg tgagctgaca     240
ctgggcctgg agccctcgga agaagggccc cccagatctc cactggctcc ctcggaaggg     300
gctggctccg atgtgtttga tggtgacctg gcaatggggg taaccaaagg gctgcagagc     360
ctctctccac atgacctcag ccctctacag cggtacagcg aggaccccac attacctctg     420
ccccccgaga ctgatggcta tgttgctccc ctggcctgca gccccagcc cgagtatgtg     480
aaccaatcag aggttcagcc tcagcctcct ttaaccccag agggtcctct gcctcctgtc     540
cggcctgctg gtgctactct agaaagaccc aagactctct ctcctgggaa gaatggggtt     600
gtcaaagacg ttttttgcctt cggggtgct gtggagaacc tgaatactt agtaccgaga     660
gaaggcactg cctctccgcc ccaccttct cctgccttca gcccagcctt tgacaacctc     720
tattactggg accagaactc atcggagcag gggcctccac caagtaactt tgaagggacc     780
cccactgcag agaaccctga gtacctaggc ctggatgtac ctgtatga                  828
```

<210> SEQ ID NO 4
<211> LENGTH: 275
<212> TYPE: PRT
<213> ORGANISM: Rat

<400> SEQUENCE: 4

```
Met Ala Ser Cys Val Asp Leu Asp Glu Arg Gly Cys Pro Ala Glu Gln
 1               5                  10                  15

Arg Ala Ser Pro Val Thr Phe Ile Ile Ala Thr Val Val Gly Val Leu
                20                  25                  30

Leu Phe Leu Ile Leu Val Val Val Gly Ile Leu Ile Lys Arg Arg
            35                  40                  45

Arg Gln Lys Ile Arg Ser Pro Thr Pro Gly Thr Gly Ser Thr Ala His
        50                  55                  60

Arg Arg His Arg Ser Ser Thr Arg Ser Gly Gly Gly Glu Leu Thr
 65                 70                  75                  80

Leu Gly Leu Glu Pro Ser Glu Glu Gly Pro Arg Ser Pro Leu Ala
                85                  90                  95

Pro Ser Glu Gly Ala Gly Ser Asp Val Phe Asp Gly Asp Leu Ala Met
               100                 105                 110

Gly Val Thr Lys Gly Leu Gln Ser Leu Ser Pro His Asp Leu Ser Pro
               115                 120                 125

Leu Gln Arg Tyr Ser Glu Asp Pro Thr Leu Pro Leu Pro Pro Glu Thr
           130                 135                 140

Asp Gly Tyr Val Ala Pro Leu Ala Cys Ser Pro Gln Pro Glu Tyr Val
145                 150                 155                 160

Asn Gln Ser Glu Val Gln Pro Gln Pro Pro Leu Thr Pro Glu Gly Pro
               165                 170                 175

Leu Pro Pro Val Arg Pro Ala Gly Ala Thr Leu Glu Arg Pro Lys Thr
           180                 185                 190

Leu Ser Pro Gly Lys Asn Gly Val Val Lys Asp Val Phe Ala Phe Gly
       195                 200                 205

Gly Ala Val Glu Asn Pro Glu Tyr Leu Val Pro Arg Glu Gly Thr Ala
   210                 215                 220
```

```
Ser Pro Pro His Pro Ser Pro Ala Phe Ser Pro Ala Phe Asp Asn Leu
225                 230                 235                 240

Tyr Tyr Trp Asp Gln Asn Ser Ser Glu Gln Gly Pro Pro Ser Asn
            245                 250                 255

Phe Glu Gly Thr Pro Thr Ala Glu Asn Pro Glu Tyr Leu Gly Leu Asp
                260                 265                 270

Val Pro Val
    275

<210> SEQ ID NO 5
<211> LENGTH: 50
<212> TYPE: PRT
<213> ORGANISM: Rat

<400> SEQUENCE: 5

Ser Cys Val Asp Leu Asp Glu Arg Gly Cys Pro Ala Glu Gln Arg Ala
1               5                   10                  15

Ser Pro Val Thr Phe Ile Ile Ala Thr Val Val Gly Val Leu Leu Phe
            20                  25                  30

Leu Ile Leu Val Val Val Gly Ile Leu Ile Lys Arg Arg Arg Gln
        35                  40                  45

Lys Ile
    50

<210> SEQ ID NO 6
<211> LENGTH: 154
<212> TYPE: DNA
<213> ORGANISM: Rat

<400> SEQUENCE: 6
tcctgtgtgg atctggatga acgaggctgc ccagcagagc agagagccag cccggtgaca     60
ttcatcattg caactgtaga gggcgtcctg ctgttcctga tcttagtggt ggtcgttgga    120
atcctaatca aacgaaggag acagaagatc cgga                                154

<210> SEQ ID NO 7
<211> LENGTH: 221
<212> TYPE: PRT
<213> ORGANISM: Rat

<400> SEQUENCE: 7

Pro Thr Pro Gly Thr Gly Ser Thr Ala His Arg Arg His Arg Ser Ser
1               5                   10                  15

Ser Thr Arg Ser Gly Gly Gly Glu Leu Thr Leu Gly Leu Glu Pro Ser
            20                  25                  30

Glu Glu Gly Pro Pro Arg Ser Pro Leu Ala Pro Ser Glu Gly Ala Gly
        35                  40                  45

Ser Asp Val Phe Asp Gly Asp Leu Ala Met Gly Val Thr Lys Gly Leu
    50                  55                  60

Gln Ser Leu Ser Pro His Asp Leu Ser Pro Leu Gln Arg Tyr Ser Glu
65                  70                  75                  80

Asp Pro Thr Leu Pro Leu Pro Pro Glu Thr Asp Gly Tyr Val Ala Pro
                85                  90                  95

Leu Ala Cys Ser Pro Gln Pro Glu Tyr Val Asn Gln Ser Glu Val Gln
            100                 105                 110

Pro Gln Pro Pro Leu Thr Pro Glu Gly Pro Leu Pro Pro Val Arg Pro
        115                 120                 125
```

```
Ala Gly Ala Thr Leu Glu Arg Pro Lys Thr Leu Ser Pro Gly Lys Asn
    130                 135                 140
Gly Val Val Lys Asp Val Phe Ala Phe Gly Ala Val Glu Asn Pro
145                 150                 155                 160
Glu Tyr Leu Val Pro Arg Glu Gly Thr Ala Ser Pro Pro His Pro Ser
                165                 170                 175
Pro Ala Phe Ser Pro Ala Phe Asp Asn Leu Tyr Tyr Trp Asp Gln Asn
            180                 185                 190
Ser Ser Glu Gln Gly Pro Pro Ser Asn Phe Glu Gly Thr Pro Thr
        195                 200                 205
Ala Glu Asn Pro Glu Tyr Leu Gly Leu Asp Val Pro Val
    210                 215                 220
```

<210> SEQ ID NO 8
<211> LENGTH: 674
<212> TYPE: DNA
<213> ORGANISM: Rat

<400> SEQUENCE: 8

```
tccggagccc tacccaggc actgggagca cagcccatag aaggcaccgc agctcgtcca      60
ccaggagtgg aggtggtgag ctgacactgg gcctggagcc ctcggaagaa gggccccca    120
gatctccact ggctccctcg aaggggctg gctccgatgt gtttgatggt gacctggcaa    180
tggggtaac caaagggctg cagagcctct ctccacatga cctcagccct ctacagcggt    240
acagcgagga ccccacatta cctctgcccc ccgagactga tggctatgtt gctcccctgg    300
cctgcagccc ccagcccgag tatgtgaacc aatcagaggt tcagcctcag cctcctttaa    360
ccccagaggg tcctctgcct cctgtccggc ctgctggtgc tactctagaa agacccaaga    420
ctctctctcc tgggaagaat ggggttgtca agacgttttt gccttcgggg ggtgctgtgg    480
agaaccctga atacttagta ccgagagaag gcactgcctc tccgcccac ccttctcctg     540
ccttcagccc agcctttgac aacctctatt actgggacca gaactcatcg gagcagggc    600
ctccaccaag taactttgaa gggaccccca ctgcagagaa ccctgagtac ctaggcctgg    660
atgtacctgt atga                                                      674
```

<210> SEQ ID NO 9
<211> LENGTH: 825
<212> TYPE: DNA
<213> ORGANISM: Homo sapiens

<400> SEQUENCE: 9

```
atggcctgtg tggacctgga tgacaagggc tgccccgccg agcagagagc cagccctctg     60
acgtccatcg tctctgcggt ggttggcatt ctgctggtcg tggtcttggg ggtggtcttt    120
gggatcctca tcaagcgacg gcagcagaag atccggagcc ctgccccggg cgctgggggc    180
atggtccacc acaggcaccg cagctcatct accaggagtg gcggtgggga cctgacacta    240
ggactggagc cctctgaaga ggaggccccc aggtctccac tggcaccctc gaaggggct    300
ggctccgatg tatttgatgg tgacctggga atggggcag ccaaggggct gcaaagcctc    360
cccacacatg accccagccc tctacagcgg tacagtgagg accccacagt accctgccc    420
tctgagactg atggctacgt tgcccccctg acctgcagcc ccagcctga atatgtgaac    480
cagccagatg ttcggcccca gccccttcg ccccgagagg gccctctgcc tgctgcccga    540
cctgctggtg ccactctgga aagggccaag actctctccc cagggaagaa tggggtcgtc    600
aaagacgttt ttgcctttgg gggtgccgtg agaaccccg agtacttgac ccccagggga    660
```

```
ggagctgccc ctcagcccca ccctcctcct gccttcagcc cagccttcga caacctctat    720
tactgggacc aggacccacc agagcggggg gctccaccca gcaccttcaa agggacacct    780
acggcagaga acccagagta cctgggtctg gacgtgccag tgtga                    825
```

<210> SEQ ID NO 10
<211> LENGTH: 275
<212> TYPE: PRT
<213> ORGANISM: Homo sapiens

<400> SEQUENCE: 10

```
Met Ala Cys Val Asp Leu Asp Asp Lys Gly Cys Pro Ala Glu Gln Arg
1               5                   10                  15

Ala Ser Pro Leu Thr Ser Ile Val Ser Ala Val Val Gly Ile Leu Leu
            20                  25                  30

Val Val Val Leu Gly Val Val Phe Gly Ile Leu Ile Lys Arg Arg Gln
        35                  40                  45

Gln Lys Ile Arg Ser Pro Ala Pro Gly Ala Gly Met Val His His
    50                  55                  60

Arg His Arg Ser Ser Thr Arg Ser Gly Gly Gly Asp Leu Thr Leu
65                  70                  75                  80

Gly Leu Glu Pro Ser Glu Glu Ala Pro Arg Ser Pro Leu Ala Pro
                85                  90                  95

Ser Glu Gly Ala Gly Ser Asp Val Phe Asp Gly Asp Leu Gly Met Gly
            100                 105                 110

Ala Ala Lys Gly Leu Gln Ser Leu Pro Thr His Asp Pro Ser Pro Leu
        115                 120                 125

Gln Arg Tyr Ser Glu Asp Pro Thr Val Pro Leu Pro Ser Glu Thr Asp
    130                 135                 140

Gly Tyr Val Ala Pro Leu Thr Cys Ser Pro Gln Pro Glu Tyr Val Asn
145                 150                 155                 160

Gln Pro Asp Val Arg Pro Gln Pro Pro Ser Pro Arg Glu Gly Pro Leu
                165                 170                 175

Pro Ala Ala Arg Pro Ala Gly Ala Thr Leu Glu Arg Ala Lys Thr Leu
            180                 185                 190

Ser Pro Gly Lys Asn Gly Val Val Lys Asp Val Phe Ala Phe Gly Gly
        195                 200                 205

Ala Val Glu Asn Pro Glu Tyr Leu Thr Pro Gln Gly Gly Ala Ala Pro
    210                 215                 220

Gln Pro His Pro Pro Ala Phe Ser Pro Ala Phe Asp Asn Leu Tyr
225                 230                 235                 240

Tyr Trp Asp Gln Asp Pro Pro Glu Arg Gly Ala Pro Pro Ser Thr Phe
                245                 250                 255

Lys Gly Thr Pro Thr Ala Glu Asn Pro Glu Tyr Leu Gly Leu Asp Val
            260                 265                 270

Pro Val Glx
        275
```

<210> SEQ ID NO 11
<211> LENGTH: 50
<212> TYPE: PRT
<213> ORGANISM: Homo sapiens

<400> SEQUENCE: 11

```
Cys Val Asp Leu Asp Asp Lys Gly Cys Pro Ala Glu Gln Arg Ala Ser
1               5                   10                  15
```

-continued

Pro Leu Thr Ser Ile Ile Ser Ala Val Val Gly Ile Leu Leu Val Val
            20                  25                  30

Val Leu Gly Val Val Phe Gly Ile Leu Ile Lys Arg Arg Gln Gln Lys
        35                  40                  45

Ile Arg
    50

<210> SEQ ID NO 12
<211> LENGTH: 151
<212> TYPE: DNA
<213> ORGANISM: Homo sapiens

<400> SEQUENCE: 12
tgtgtggacc tggatgacaa gggctgcccc gccgagcaga gagccagccc tctgacgtcc      60
atcgtctctg cggtggttgg cattctgctg gtcgtggtct tgggggtggt ctttgggatc     120
ctcatcaagc gacggcagca gaagatccgg a                                    151

<210> SEQ ID NO 13
<211> LENGTH: 224
<212> TYPE: PRT
<213> ORGANISM: Homo sapiens

<400> SEQUENCE: 13

Cys Pro Asp Pro Ala Pro Gly Ala Gly Gly Met Val His His Arg His
1               5                   10                  15

Arg Ser Ser Thr Arg Ser Gly Gly Gly Asp Leu Thr Leu Gly Leu
            20                  25                  30

Glu Pro Ser Glu Glu Ala Pro Arg Ser Pro Leu Ala Pro Ser Glu
        35                  40                  45

Gly Ala Gly Ser Asp Val Phe Asp Gly Asp Leu Gly Met Gly Ala Ala
    50                  55                  60

Lys Gly Leu Gln Ser Leu Pro Thr His Asp Pro Ser Pro Leu Gln Arg
65                  70                  75                  80

Tyr Ser Glu Asp Pro Thr Val Pro Leu Pro Ser Glu Thr Asp Gly Tyr
                85                  90                  95

Val Ala Pro Leu Thr Cys Ser Pro Gln Pro Glu Tyr Val Asn Gln Pro
            100                 105                 110

Asp Val Arg Pro Gln Pro Pro Ser Pro Arg Glu Gly Pro Leu Pro Ala
        115                 120                 125

Ala Arg Pro Ala Gly Ala Thr Leu Glu Arg Pro Lys Thr Leu Ser Pro
    130                 135                 140

Gly Lys Asn Gly Val Val Lys Asp Val Phe Ala Phe Gly Gly Ala Val
145                 150                 155                 160

Glu Asn Pro Glu Tyr Leu Thr Pro Gln Gly Gly Ala Ala Pro Gln Pro
                165                 170                 175

His Pro Pro Pro Ala Phe Ser Pro Ala Phe Asp Asn Leu Tyr Tyr Trp
            180                 185                 190

Asp Gln Asp Pro Pro Glu Arg Gly Ala Pro Pro Ser Thr Phe Lys Gly
        195                 200                 205

Thr Pro Thr Ala Glu Asn Pro Glu Tyr Leu Gly Leu Asp Val Pro Val
    210                 215                 220

<210> SEQ ID NO 14
<211> LENGTH: 679
<212> TYPE: DNA
<213> ORGANISM: Homo sapiens -continued

```
<220> FEATURE:
<221> NAME/KEY: misc_feature
<222> LOCATION: (9)..(9)
<223> OTHER INFORMATION: n represents a site specific a to g mutation
      induced to create the BspE1 site for fusion

<400> SEQUENCE: 14
ttctgtccng agccctgccc cgggcgctgg gggcatggtc caccacaggc accgcagctc      60
atctaccagg agtggcggtg gggacctgac actagggctg gagccctctg aagaggaggc    120
ccccaggtct ccactggcac cctccgaagg ggctggctcc gatgtatttg atggtgacct    180
gggaatgggg gcagccaagg ggctgcaaag cctcccaca catgacccca gccctctaca     240
gcggtacagt gaggacccca cagtacccct gccctctgag actgatggct acgttgcccc    300
cctgacctgc agcccccagc ctgaatatgt gaaccagcca gatgttcggc cccagccccc    360
ttcgccccga gagggccctc tgcctgctgc ccgacctgct ggtgccactc tggaaagggc    420
caagactctc tccccaggga agaatggggt cgtcaaagac gtttttgcct ttgggggtgc    480
cgtggagaac cccgagtact tgacacccca gggaggagct gcccctcagc cccaccctcc    540
tcctgccttc agcccagcct tcgacaacct ctattactgg gaccaggacc accagagcg     600 ggggctcca  cccagcacct tcaaagggac acctacggca gagaacccag agtacctggg    660
tctggacgtg ccagtgtga                                                  679
```

HER2/NEU TARGET ANTIGEN AND USE OF SAME TO STIMULATE AN IMMUNE RESPONSE

CROSS REFERENCE TO RELATED APPLICATIONS

This application claims the benefit of priority under 35 USC § 119 of International Application No. PCT/US02/22975, with an international filing date of Jul. 18, 2002, which claims priority to U.S. Ser. No. 60/306,250, filed Jul. 18, 2001, which is incorporated herein by reference in its entirety.

FIELD OF THE INVENTION

The invention relates generally to a tumor vaccine and a method of stimulating an immune response against a tumor, and more specifically to an antigenic peptide encoded by a recombinant Her2/neu polynucleotide sequence, to a genetic vaccine containing the recombinant Her2/neu polynucleotide sequence, to a vector containing such a polynucleotide, and to methods of stimulating an immune response in a human patient against a tumor expressing Her2/neu.

BACKGROUND INFORMATION

Although great advances have been made in the methods used for treating cancer patients, significant problems remain. In general, cancer is treated using surgery, chemotherapy, radiation therapy, or a combination of these methods. Surgical methods, however, can be curative only when the cancer detected early and has not metastasized. Similarly, radiotherapy, when used, generally only is effective when a tumor is localized. In many cases, however, a cancer has metastasized by the time it has been diagnosed and, therefore, chemotherapy, which provides a systemic treatment, is indicated, sometimes in combination with surgery or radiotherapy. In most cases, chemotherapy suffers from the disadvantage that it generally is not specific for the cancer cells, but also kills rapidly dividing normal cells. In fact, toxicity to normal cells generally limits the dose of chemotherapy that a patient can tolerate. In other cases, a hormonal therapy can provide a more specific treatment, for example, for treating breast cancer where the breast cancer cells express an estrogen receptor. However, cancer cells often become resistant to a chemotherapeutic, including hormonal, agent and, therefore, become refractory to the treatment.

Immunotherapy holds great promise for treating cancer because it can be effective against disseminated disease and because, in theory, it can directed only against the cancer cells. Immunotherapy can be active or passive. For active immunotherapy, a tumor antigen is administered to a patient, resulting in the generation of an immune response against the antigen and against cancer cells expressing the antigen. For passive immunotherapy, an antibody against a tumor antigen, for example, is raised separate from the patient, and is administered to a patient having a cancer that expresses the antigen used to raise the antibody.

Efforts at active immunotherapy of melanoma, for example, have been attempted using crude vaccines composed of "killed" melanoma cells isolated either from the patient to be treated or from another patient, or of lysates or extracts of such cells. However, the use of crude vaccines for immunotherapy is problematic, in part, because the precise antigenic composition of such vaccines is largely undefined. It is generally believed that more effective immunotherapy requires the identification and isolation of proteins that are expressed relatively specifically by cancer cells, preferably on their surface, but are not expressed on normal cells. However, such cancer cell specific antigens are rare and have been difficult to identify.

Many cancers are characterized, in part, by an overexpression of an otherwise normal protein, and efforts to target these overexpressed proteins using immunotherapeutic methods have been attempted. For example, the Her2/neu protein can be overexpressed in breast cancer cells, and passive immunotherapy using a monoclonal anti-Her2/neu antibody, Herceptin® antibody, has shown a clinical benefit. However, the use of Herceptin® antibody can result in the development of ventricular dysfunction and congestive heart failure and, therefore, requires careful monitoring of a treated patient. Such methods of passive immunotherapy also have inherent problems. For example, administration of an antibody as a passive immunotherapy procedure can result in an immune response generated by the patient against the administered antibody and can result in an anaphylactic reaction. Also, an administered antibody has a finite lifetime in a patient and, therefore, must be administered several times over a course of treatment. As such, active immunotherapy against a protein expressed by a cancer cell would be a preferred method of cancer treatment. Unfortunately, as discussed above, few cancer specific proteins have been described. Thus, a need exists to identify tumor antigens that can be used to stimulate an active immune response by a patient against the cancer, without producing undesirable toxicity to normal cells in the patient. The present invention satisfies this need and provides additional advantages.

SUMMARY OF THE INVENTION

The present invention relates to a recombinant polynucleotide encoding a Her2/neu target antigen that includes at least a first nucleotide sequence, which encodes a Her2/neu target antigen having an amino acid sequence corresponding to about amino acid residues 634 to 683 operatively linked to amino acid residues 1035 to 1225 of SEQ ID NO:1, or to about amino acid residues 635 to 685 operatively linked to amino acid residues 1037 to 1257 of SEQ ID NO:2. The present invention also relates to a recombinant polynucleotide encoding a Her2/neu target antigen that includes at least a first nucleotide sequence, which encodes a Her2/neu target antigen consisting of an amino acid sequence corresponding to amino acid residues 606 to 683 operatively linked to amino acid residues 1035 to 1255 of SEQ ID NO:1, or to amino acid residues 608 to 685 operatively linked to amino acid residues 1037 to 1257 of SEQ ID NO:2. Recombinant polynucleotides of the invention are exemplified by a polynucleotide encoding the amino acid sequence set forth in SEQ ID NO:4 or SEQ ID NO:10, and by a polynucleotide having the nucleotide sequence set forth in SEQ ID NO:3 or SEQ ID NO:9.

A recombinant polynucleotide of the invention can further include a second nucleotide sequence, which is operatively linked to the first nucleotide sequence encoding the Her2/neu target antigen. The second nucleotide sequence can include an expression regulatory element, for example, a transcriptional regulatory element, a translational regulatory element, or a combination thereof, or can encode a heterologous amino acid sequence. Accordingly, a recombinant polynucleotide of the invention can encode a fusion protein containing a Her2/neu target antigen and a heterologous amino acid sequence. The heterologous amino acid sequence can be a peptide or polypeptide, which can be useful, for example, as a tag to detect or isolate the fusion protein containing the Her2/neu target antigen, or as a immunostimulatory polypeptide to further stimulate an immune response stimulated by the Her2/neu target antigen. A recombinant polynucleotide of the invention can be contained in a cell, which can be a prokaryotic or eukaryotic cell, including a mammalian cell.

The present invention also relates to a vector, which contains a recombinant polynucleotide encoding a Her2/neu target antigen, which has an amino acid sequence corresponding to about amino acids 634 to 683 operatively linked to amino acids 1035 to 1255 of SEQ ID NO:1, or to about amino acids 635 to 685 operatively linked to amino acids 1037 to 1257 of SEQ ID NO:2, or which corresponds an amino acid sequence consisting of amino acid residues 606 to 683 operatively linked to amino acid residues 1035 to 1255 of SEQ ID NO:1, or consisting of amino acid residues 608 to 685 operatively linked to amino acid residues 1037 to 1257 of SEQ ID NO:2. The vector can be an expression vector, which contains replication or expression regulatory elements necessary for propagation of the vector or expression of the encoded Her2/neu target antigen or both in a prokaryotic or eukaryotic cell, for example, a mammalian cell. The vector can be a plasmid vector or a viral vector, including a viral vector plasmid. In one embodiment, the viral vector is an alphavirus vector, for example, a Venezuelan equine encephalitis virus (VEE) vector. In another embodiment, the viral vector is a retrovirus vector, an adenovirus vector, an adeno-associated virus vector, or a vaccinia virus vector. Also provided is a host cell containing a vector of the invention, such a host cell being useful, for example, for propagating the vector or for expressing an encoded Her2/neu target antigen. Where the vector is a viral vector, the host cell can be a helper cell, which provides in trans factors necessary for replication and packaging of viral particles containing the viral vector.

The present invention further relates to a pharmaceutical composition, which contains a recombinant polynucleotide encoding a Her2/neu target antigen having an amino acid sequence corresponding to amino acids 634 to 683 operatively linked to amino acids 1035 to 1255 of SEQ ID NO:1, or to amino acids 635 to 685 operatively linked to amino acids 1037 to 1257 of SEQ ID NO:2, or which contains a recombinant polynucleotide encoding a Her2/neu target antigen consisting of an amino acid sequence corresponding to amino acid residues 606 to 683 operatively linked to amino acid residues 1035 to 1255 of SEQ ID NO:1, or to amino acid residues 608 to 685 operatively linked to amino acid residues 1037 to 1057 of SEQ ID NO:2. Such a composition is useful, for example, as a genetic vaccine. In such a composition, the recombinant polynucleotide can, but need not, be contained in a vector, which can be an expression vector, including a viral expression vector. In one embodiment, the encoded Her2/neu target antigen has an amino acid sequence as set forth in SEQ ID NO:4. In another embodiment, the encoded Her2/neu target antigen has an amino acid sequence that corresponds to SEQ ID NO:4, for example, a corresponding amino acid sequence of a mammalian Her2/neu homolog such as a human Her2/neu homolog (see SEQ ID NO:10).

The present invention also relates to a recombinant polypeptide, which includes a Her2/neu target antigen having an amino acid sequence corresponding to about amino acid residues 634 to 683 operatively linked to amino acids 1035 to 1255 of SEQ ID NO:1, or to about amino acids 635 to 685 operatively linked to amino acids 1037 to 1257 of SEQ ID NO:2, or which consisting of an amino acid sequence corresponding to amino acid residues 606 to 683 operatively linked to amino acid residues 1035 to 1255 of SEQ ID NO:1, or to amino acid residues 608 to 685 operatively linked to amino acid residues 1037 to 1257 of SEQ ID NO:2. The recombinant polypeptide can have a Her2/neu target antigen amino acid sequence as set forth in SEQ ID NO:4, or an amino acid sequence corresponding to SEQ ID NO:4, particularly an amino acid sequence derived from a mammalian Her2/neu protein, for example, a Her2/neu target antigen as set forth in SEQ ID NO:10.

A recombinant polypeptide of the invention can contain a heterologous amino acid sequence operatively linked to the Her2/neu target antigen. The heterologous amino acid sequence can be any sequence other than an amino acid sequence that is contiguous in a wild type Her2/neu protein to the amino acid sequences that are operatively linked to form a Her2/neu target antigen of the invention. As such, the heterologous amino acid sequence can be a peptide or polypeptide, for example, an immunostimulatory polypeptide such as a costimulatory B7 molecule, or a cytokine such as an interleukin or an interferon. Also provided is a pharmaceutical composition containing a recombinant polypeptide of the invention.

The present invention also relates to a method for expressing a Her2/neu target antigen in a cell. Such a method can be performed, for example, by contacting the cell with a recombinant polynucleotide encoding a Her2/neu target antigen of the invention, for example, a Her2/neu target antigen having the amino acid sequence set forth in SEQ ID NO:4 or SEQ ID NO:10, under conditions that allow expression of the Her2/neu target antigen by the cell. The contacting can be performed on any cell in which the Her2/neu target antigen can be expressed, including prokaryotic and eukaryotic cells, for example, a mammalian cell. Furthermore, the contacting can be on a cell in culture, for example, a cell that has been established for passage in culture or a panel of such cells, or a cell that has been removed from the subject and is contacted ex vivo; or the contacting can be performed in vivo, in which case the recombinant polynucleotide can be administered to the site of cell or to a site to which the cell can migrate, or can be administered systemically such that it can circulate to the cells in which the Her2/neu target antigen is expressed.

In a method for expressing a Her2/neu target antigen in a cell, the recombinant polynucleotide can, but need not, be contained in a vector. Where the recombinant polynucleotide is contained in vector, the vector can be a plasmid or viral vector, and can be a cloning or expression vector. In one embodiment, the vector is an expression vector, and in another embodiment, the vector is a viral expression vector. In addition, the recombinant polynucleotide can, but need not, be operatively linked to an expression regulatory element, for example, a transcriptional regulatory element such as a tissue specific or inducible transcriptional regulatory element, or a translational regulatory element such as an internal ribosome binding site.

A method of expressing a Her2/neu target antigen in a cell can further include a step of isolating the Her2/neu target antigen from the cell. The Her2/neu target antigen can be isolated from the cell using any convenient method, including a method based on the identification or binding of a polypeptide operatively linked to the Her2/neu target antigen, for example, a polyhistidine tag peptide, which can be bound by a nickel ion chelate. Accordingly, the present invention provides an isolated Her2/neu target antigen obtained by such a method.

In addition, a method of expressing a Her2/target antigen in a cell can further include a step of isolating the cell expressing the Her2/neu target antigen. Such cell can be isolated, for example, by performing a limiting dilution preparation of cells contacted with the recombinant polynucleotide, and selecting cells in which the encoded Her2/neu target antigen is expressed. Accordingly, the present invention provides an isolated cell, which expresses the Her2/neu target antigen, which is obtained by such a method.

The present invention also relates to a method of stimulating an immune response in a subject against cancer cells that express Her2/neu. Such a method can be performed, for example, by contacting cells with the recombinant polynucleotide of the invention under conditions that allow expression from the recombinant polynucleotide of the Her2/neu target antigen in the cells and contact of the expressed Her2/neu target antigen with immunoeffector cells, which are involved in an immune response, in the subject. The recombinant polynucleotide can, but need not, be contained in a vector, which can be, for example, a viral vector.

In one embodiment of the method of stimulating an immune response, cells are contacted with the recombinant polynucleotide in culture, to generate cells expressing the Her2/neu target antigen, which are administered to the subject, thereby stimulating an immune response in the subject against cancer cells that express Her2/neu. The cells that are contacted with the target antigen can, but need not, be antigen presenting cells (APCs) such as dendritic cells. When the cells are not APCs, the expressed Her2/neu target antigen generally comprises a fusion protein that can be secreted from the cell expressing the target antigen.

In another embodiment of the method, cells other than immunoeffector cells are contacted with the recombinant polynucleotide in culture, to generate cells that express the Her2/neu target antigen, which are further contacted in culture with immunoeffector cells to generate stimulated immunoeffector cells, for example, APCs that can process and present the target antigen to other immunoeffector cells. The stimulated cells, either alone or in combination with the cells that express the Her2/neu target antigen, then are administered to the subject, thereby stimulating an immune response in the subject against cancer cells that express Her2/neu. The cells that are contacted with the recombinant polynucleotide and express the Her2/neu target antigen, or the immunoeffector cells, or both, can be autologous cells, which are obtained from the subject to be treated, or can be allogeneic cells with respect to the subject, including, for example, cells that are haplotype matched with respect to major histocompatibility loci. In still another embodiment, the method of stimulating an immune response is performed by contacting the subject's cells with the recombinant polynucleotide in vivo, wherein the cells, which express the Her2/neu target antigen, can further contact immunoeffector cells, thereby stimulating an immune response in the subject against cancer cells expressing Her2/neu.

The present invention also relates to a method of immunostimulating immunoeffector cells against cancer cells expressing Her2/neu by contacting cells involved in the immune response with a recombinant polypeptide of the invention. The immunoeffector cells, which are contacted with the recombinant polypeptide, can be any cells that can be immunostimulated due to contact with the recombinant polypeptide, particularly APCs such as dendritic cells, B cells, and the like. The contacting can be performed on cells in culture, or can be performed in vivo by administering the recombinant polypeptide to the subject. The cancer cells, against which the immune response is stimulated, can be any cancer cells that express Her2/neu, particularly cancer cells that overexpress Her2/neu as compared to the level of Her2/neu expressed by normal cells of the type from which the cancer cells are derived. It should be recognized that a method of the invention also can be used to stimulate an immune response against any cells that express Her2/neu, and particularly against cells that overexpress Her2/neu and are involved in a pathologic condition.

A method of immunostimulating immunoeffector cells against cancer cells expressing Her2/neu can further include a step of isolating the immunostimulated immunoeffector cells. Accordingly, the present invention also provides a method of isolating a Her2/neu target antigen immunostimulated cell, and provides an isolated immunostimulated cell obtained by such a method, for example, an isolated immunostimulated dendritic cell.

The present invention also relates to a method of making a target antigen, which can stimulate an immune response against a protein expressed on the surface of a cancer cell. Such a method can be performed, for example, by selecting a first peptide portion of the protein, wherein the first peptide portion includes the transmembrane domain and has limited homology to proteins other than the protein expressed on the surface of the tumor cell; selecting a second peptide portion of the protein, which includes a portion of the cytoplasmic domain of the protein and has limited homology to proteins other than the protein expressed on the surface of the tumor cell; and operatively linking the first peptide portion and the second peptide portion, thereby making the target antigen.

BRIEF DESCRIPTION OF THE DRAWINGS

FIGS. 1A and 1B show the amino acid sequences for the human (h; SEQ ID NO:1) and rat (r; SEQ ID NO:2) Her2/neu proteins. In the rat Her2/neu sequence (SEQ ID NO:2), only those amino acid residues that differ from those in the human sequence (SEQ ID NO:1) are shown. Bold indicates the transmembrane domain. Underlining indicates the sequences used to prepare a Her2/neu target antigen.

FIGS. 6A and 6B show nucleotide (SEQ ID NO:3; start to stop codon) and amino acid (SEQ ID NO:4) sequences of a Her2/neu target antigen, which includes two peptide portions of rat Her2/neu (i.e., amino acid residues 635 to 685 and 1037 to 1257 of SEQ ID NO:2; see, also, Entrez P06494, and SEQ ID NOS:5 and 7), which are operatively linked through a serine residue (single underline) and encoded by a portion of the BspE1 restriction endonuclease recognition site (single underline) that was engineered into the polynucleotides comprising the encoding recombinant polynucleotide. Double underlining indicates sequence added to initiate transcription and maintain reading frame. Single underline indicates the fusion site (note: a terminal adenine residue was added to the "Proximal rat Her2/neu nucleotide sequence (SEQ ID NO:6; see, also GenBank Nucleotide Acc. No. NM_017003-nucleotides 1928 to 2081) to generate a BspE1 site; underlined). The construction process also added a serine (S) to the amino acid residues 638-688 of the "Proximal rat Her2/neu polypeptide" (SEQ ID NO:5; Entrez P06494, amino acid residues 635 to 685; see, also, GenBank Protein Acc. No. NP_058699, amino acid residues 638 to 688—sequences identical in these regions). The "Terminal rat Her2/neu polypeptide" (SEQ ID NO:7 (amino acids 1037-1257 of Entrez P0649; see also, GenBank Protein Acc. No. NP_058699, amino acid residues 1040 to 1260—identical sequences in these regions); and the "Terminal rat Her2/neu nucleotide sequence (SEQ ID NO:8; GenBank Nucleotide Acc. No. NM_017003, nucleotides 3128 to 3799; note: introduced BspE1 site underlined—"G" residue added to maintain reading frame of fusion target antigen) also are shown.

FIGS. 7A and 7B show the nucleotide (SEQ ID NO:9) and amino acid (SEQ ID NO:10) sequences for the "HUMAN Her2/neu" target antigen. Underline and double underlining as in FIGS. 6A and 6B. Similarly to FIGS. 6A and 6B, the proximal and terminal Her2/neu sequence used to construct the fusion target antigen are shown. "Proximal human Her2/neu polypeptide" (SEQ ID NO:11; Entrez NP_004439 or P04626, amino acid residues 634 to 683) and "Proximal human Her2/neu nucleotide" (SEQ ID NO:12; GenBank Nucleotide Acc. No. NM_004448, nucleotides 2040 to 2199) are shown, as are the "Distal human Her2/neu" polypeptide (SEQ ID NO:13; Entrez NP 004439 or P04626, amino acid residues 1034-1255) and "Distal human Her2/neu nucleotide (SEQ ID NO:14; GenBank Nucleotide Acc. No. NM_004448, nucleotides 3253 to 3918) sequences. In SEQ ID NO:14, "a/g" represents a site specific (a to g) mutation induced to create the BspE1 site for fusion. "G" indicates a guanine residue added to maintain the reading frame of the fusion target antigen.

DETAILED DESCRIPTION OF THE INVENTION

Figure 2:
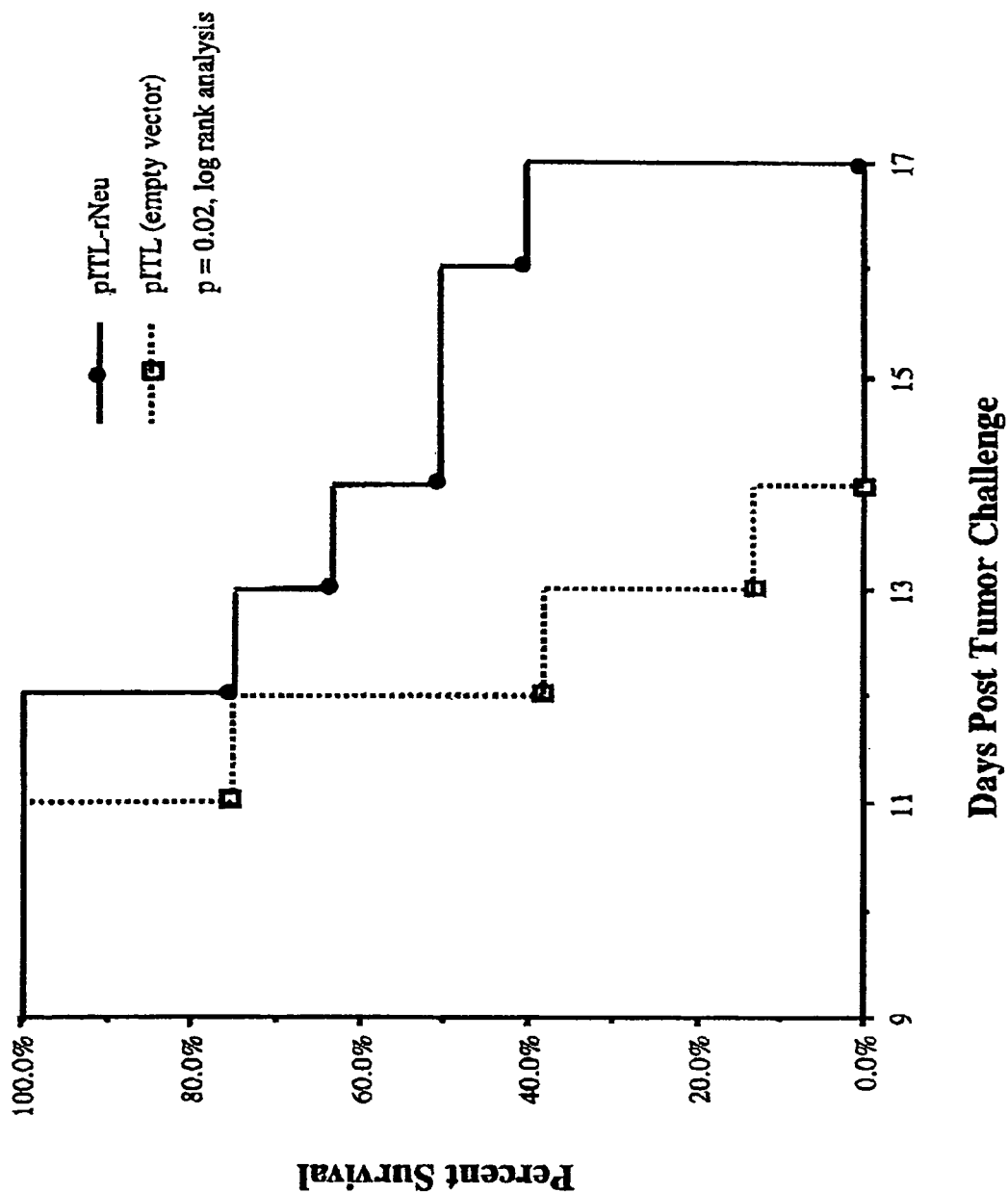
FIG. 2 compares the percent survival (ordinate) with time after tumor cell challenge (abscissa) of Fisher 344 rats vaccinated with a vector containing a Her2/neu target antigen (pITL-rNeu) and rats vaccinated with an empty vector (pITL). Vaccinations were administered every 3 weeks. Tumor challenge occurred 4 weeks after the last vaccination. Both lines represent administration of 100 ug of DNA/injection. Animals were euthanized when tumors reached a maximum dimension of 2.5 cm. Survival differences were statistically significant by log rank analysis, $p=0.02$.

The present invention provides compositions useful for stimulating an immune response against cancer cells that express a Her2/neu protein, and also provides methods of using the compositions to stimulate such an immune response. As disclosed herein, the compositions of the invention include, or encode, a recombinant polypeptide (Her2/neu target antigen) formed by linking two non-contiguous peptide portions of Her2/neu such that they are expressed as a single polypeptide. Her2/neu is a member of the epidermal growth factor receptor family of proteins and is normally expressed in various cell types. In addition, Her2/neu is over-expressed in various types of cancer, including in about 20 to 30% of breast cancers, in adenocarcinomas of the ovary, salivary gland, stomach and kidney, in colon cancers, and in non-small cell lung cancer (see, for example, Fendly et al., *J. Biol. Resp. Mod.* 9:449-455, 1990, which is incorporated herein by reference).

Since Her2/neu is a "self" protein, it is not normally recognized by the immune system, and any robust immune response generated against a normal Her2/neu protein is likely to elicit deleterious crossreactive autoimmune phenomena. As such, efforts have been made to identify peptide antigens of Her2/neu that can be used to stimulate an immune response against Her2/neu expressing tumor cells in a cancer patient. For use as a cancer vaccine, it is preferable if the target antigen elicits a T helper-1 (Th1) cell response and a cytotoxic T lymphocyte (CTL) response. Such an immune response is generally observed for proteins expressed in the intracellular compartment, and less prominently with extracellular or secreted proteins. In addition, rapid degradation of a protein can contribute to establishing such a bias in the immune response, facilitating antigen presentation and, perhaps, assisting in establishing specificity of the immune response (see, for example, Montoya and Del Val, *J. Immunol.* 163:1914-1922, 1999; Yewdell et al., *Adv. Immunol.* 73:1-77, 1999). Although peptide strategies can be used to obtain such a biased immune response, the occurrence of antigen loss variants (Marincola et al., *Adv. Immunol.* 74:181-273, 2000; Riker et al., *Surgery* 126:112-120, 1999; Slingluff et al., *Cancer Immunol. Immunother.* 48:661-672, 2000) indicates that broader or poly-epitope immune responses will be more efficacious. Accordingly, an effort was made to design a Her2/neu target antigen that preferentially stimulates a broad based Th1 and CTL immune response.

As disclosed herein, a Her2/neu target antigen was derived by identifying two peptide portions of the human Her2/neu protein that demonstrated the lowest degree of sequence homology with other known normal human proteins. These two peptides include one peptide encompassing the transmembrane (TM) domain and a portion of the extracellular domain and a second peptide including the C-terminal domain (see FIG. 1, underlining). These sequences were combined to encode a single polypeptide that did not show any new homology to normal proteins (see Example 1). As such, a Her2/neu target antigen of the invention minimizes the likelihood that any potential crossreactive autoimmune response will occur, while maximizing specificity of the elicited immune response. Furthermore, since the Her2/neu target antigen is constructed predominantly of Her2/neu sequences that are intracellular, and represents a truncated or partial protein sequence, it can be rapidly degraded by intrinsic antigen processing to produce T cell epitopes that are presented in the context of MHC class I and, therefore, available for CTL recognition.

The use of a Her2/neu target antigen of the invention, either as a polynucleotide or as a polypeptide, to stimulate an immune response provides the advantage that specific peptide T cell epitopes that bind particular MHC class I alleles need not be defined. As compared to T cell epitopes, the Her2/neu target antigen of the invention can stimulate a more broad based and less restricted immune response than can a T cell epitope peptide. In addition, the larger polypeptide allows for the intrinsic antigen processing machinery to generate appropriate peptides for the expressed MHC alleles. To otherwise generate such peptides, all of the MHC alleles for a patient would need to be known, and the appropriate peptides would have to be characterized for any single protein antigen. The use of a Her2/neu target antigen of the invention also provides advantages over the use of a full length polypeptide antigen, which can generate a less specific immune response, more crossreactive and potentially deleterious immune reactivity, and less of a Th1 CTL bias.

Class I MHC molecules are, or can be, expressed by all nucleated cells and present T cell epitopes to cytotoxic T lymphocytes (CTLs). In general, the epitopes presented by class I MHC molecules are produced by proteolysis of endogenously expressed proteins, including proteins expressed in virally infected cells and in tumor cells. The epitope likely associates with the class I molecule in the endoplasmic reticulum, then the complex is transported to the cell surface. CTLs, which express the CD8 surface antigen ("CD8$^+$") and a CTL receptor, then bind the epitope associated with the class I molecule, thereby activating the effector function of the CTLs (see, generally, Kuby, "Immunology" 3d ed. (W.H. Freeman and Co., 1997).

Class II MHC molecules, which are expressed by antigen presenting cells, present a T cell epitope to helper T cells ("Th cells"), stimulating the Th cells, such stimulation being effective in immunity to tumors (see Abbas et al., "Cellular and Molecular Immunology," second ed. (W.B. Saunders Co. 1995); Kuby, supra, 1997). The epitopes that are bound by class II molecules generally are derived by proteolysis of exogenous proteins, which are internalized in the APC by phagocytosis or endocytosis. In addition, APCs, such as macrophages, can express co-stimulatory B7 molecules B7-1 (CD80) and B7-2 (CD86), which are recognized by a cell surface molecule (CD28) that is expressed by certain T cells, including naive T cells, and is involved in activation of the T cells. Binding of a T cell epitope and B7 molecule by Th cells stimulates activation of two subsets of Th cells, Th1 cells, which express interleukin-2 (IL-2), interferon-γ, tumor necrosis factor-β and tumor necrosis factor-α and are involved in the cell-mediated immune functions, including activation of CTLs, and Th2 cells, which secrete IL-4, IL-5, IL-6 and IL-10 and are involved in the activation of B cells (see Kuby, supra, 1997; chaps. 1, 10 and 12).

In 2000, over 184,000 new cases of breast cancer will be diagnosed, accompanied by over 41,000 deaths due to this malignancy. Although significant progress has been made in the surgical, radiotherapeutic, and medical treatment of this disease, none of these modalities, alone or in combination, provides curative therapy for the majority of patients with advanced breast cancer. Interestingly, patients with significant inflammatory infiltrates in the primary tumor (medullary carcinoma) have significantly improved survival despite a higher degree of cellular anaplasia. Elution of antigens from immune complexes present in sera of patients with breast carcinoma reveals multiple oncogenic antigens (Croce et al., *Cancer Immunol. Immunother.* 40:132-137, 1995, which is incorporated herein by reference). Breast cancer patients have been reported to have antibodies to mutated p53 proteins and Her2/neu (Angelopoulou et al., *Clin. Biochem.* 33:53-62, 2000; Disis et al., *Clin. Cancer Res.* 6:1347-1350, 2000, each of which is incorporated herein by reference). Patients with breast cancer can have a cellular response to autologous tumor associated antigens (TAAs) such as; mutated p53, HER2/neu, the MUC-1 antigen and sialyl-Tn (Disis et al., supra, 2000; Sandmajer et al., *J. Immunother.* 22:54-66, 1999). These findings, in addition to the association of improved survival with inflammatory infiltration of primary breast tumors, demonstrate that patients can mount an immune response to the malignant cells of breast tumors. As such, it is reasonable to hypothesize that a robust, antigen-specific immunotherapeutic strategy for breast cancer can have clinical efficacy.

TAAs are generally recognized by the immune system as small fragments of proteins presented to the immune system in the context of major histocompatibility complex (MHC) molecules on the surface of antigen presenting cells and tumor cells rather than as large intact proteins. Cytotoxic T lymphocytes (CTL) respond to antigens presented on MHC class I. Helper T lymphocytes respond to antigens presented on MHC class II. Anti-tumor immune responses can be broadly classified into Th1-biased and Th2-biased immune responses. Th1-biased responses support the CTL component of the cellular immune response, and Th2-biased responses support the humoral arm. In selected tumor systems, humoral (antibody) responses have had some clinical utility. In breast cancer patients, therapeutic administration of an antibody to the Her2/neu molecule, Herceptin® antibody, has resulted in clinical responses. However, these clinical responses appear to be a result of interference with receptor signaling rather than immunologically-mediated cellular destruction. Although there is a theoretical role for antibodies in the anti-tumor immune response, immunotherapeutic strategies that can elicit Th1-biased immune responses seem most likely to result in the immunological destruction of tumor cells.

The selection of a potential target TAA can substantially influence the type and class of immune response, the specificity, and potential efficacy of an immunotherapeutic strategy. TAAs containing extracellular components can be targets for humoral immune responses. However, most characterized TAAs are intracellular proteins and are unavailable for reacting with circulating antibodies. Furthermore, intracellular proteins are thought to be presented primarily on MHC class 1 and elicit CD 8+ T cell responses. In order to obtain optimal specificity, the selection of a putative target sequence within a TAA should avoid regions with a high degree of homology to other family members or other normal cellular proteins. Additionally, the immune system avoids anti-self reactivity by negative selection and the induction of peripheral tolerance to widely distributed self antigens/epitopes and this suggests that epitopes from regions of high homology are less likely to be recognized by the immune system. Thus, selection of intracellular components should bias the elicited response toward a CTL/Th 1 immune response and avoidance of these regions of high homology should enhance the potential for eliciting efficacious antigen-specific immune responses. The recent recognition of "antigen loss variants" resulting in tumor escape from single antigen immunotherapeutic strategies (Slingluff et al., supra, 2000; Riker et al., supra, 1999) suggests that the use of polyvalent (multiple antigen) immunotherapies will be necessary for optimal clinical efficacy. Among currently available technologies, genetic or molecular vaccines appear to be the most efficient for generating individualized polyvalent (multiple TAAs) immunotherapeutic strategies.

Although immune responses to various TAAs have been elicited by a number of immunotherapeutic modalities the magnitude of these responses are markedly less than those elicited by pathogenic organisms or in allogeneic graft rejection. Furthermore, using MHC tetramer staining with immunodominant peptide antigens in the setting of patients with melanoma, "antigen educated T lymphocytes" can be identified and have been recognized to be functionally anergic, suggesting that the immune system is "crippled" with regard to its recognition of TAAs (Valmori et al., *Internatl. Immunol.* 11:1971-1980, 1999; Lotze, in "Keystone Symposia on Cellular Immunity and Immunotherapy of Cancer (Santa Fe N. Mex. 2000), each of which is incorporated herein by reference). Thus, new immunotherapeutic approaches will need to include strategies to overcome what amounts to a "high activation barrier" for mounting an effective anti-tumor immune response.

One point of attack for enhancing the immune response to a specific antigen is at the initial point of presentation of antigen to the immune system. Numerous strategies have been developed for augmenting the capacity for presentation of TAAs to the immune system. The use of cytokine "biological adjuvants" such as GM-CSF has resulted in augmented immune responses, although improved clinical responses in humans have not yet been rigorously demonstrated. Another strategy has used viral vectors containing the TAA and costimulatory molecules, with or without cytokines, in order to make any transfected cell into a potent antigen presenting cell. This strategy has produced an improved magnitude of immune responses in animal models. Other strategies have focused on the most potent antigen presenting cell (APC) within the immune system in an effort to improve the magnitude of the elicited immune response, the dendritic cell (DC).

DCs can be quite pleiotropic and manifest several phenotypes, including immature and mature phenotypes (Nelson et al., *FASEB J.* 13:2021-2030, 1999, which is incorporated herein by reference). DCs express high levels of co-stimulatory and MHC molecules that are further up-regulated upon acquisition of the mature phenotype (CD83+ in humans). DCs with the immature phenotype reside in the periphery and are very active in antigen uptake and processing. In contrast, DCs with the mature phenotype are found almost exclusively in secondary lymphoid organs, where they have down-regulated their antigen uptake and processing pathways while having markedly enhanced their immunostimulatory capacity.

Various strategies have been used for loading DCs with TAAs in the ex vivo setting. DCs have been loaded with peptides from specific TAAs known to bind particular HLA molecules (Fong and Engleman, *Ann. Rev. Immunol.* 18:245-273, 2000, which is incorporated herein by reference). However, this strategy is complicated by the recently described, potentially unfavorable kinetics of peptide degradation by DCs. DCs have been fused with tumor cells and transfected with amplified tumor-derived mRNA or cDNA. These latter efforts, although targeting multiple TAAs, have the disadvantage of lacking the ability to define and monitor antigen-specific responses because the specific antigens are not necessarily known. Thus, monitoring of anti-tumor immune responses must rely upon the most general measures of immune responses and upon clinical outcome. DCs have also been transfected with viral constructs, with successful expression of the encoded TAA, induction of an antigen-specific immune response and spontaneous acquisition of the mature phenotype. However, this strategy and most of the others involve adoptive transfer of ex vivo manipulated DCs of the mature phenotype. Trafficking of adoptively transferred DCs has been problematic with scant evidence that the DCs traffic appropriately to either secondary lymphoid organs or sites of tumor (Barratt-Boyes et al., *J. Immunol.* 164:2487-2495, 2000; Morse et al., *Cancer Res.* 59:56-58, 1999, each of which is incorporated herein by reference). The capacity to load or transfect DCs of the immature phenotype with specific TAAs in vivo would circumvent the limitations noted above.

Venezuelan Equine Encephalitis (VEE) virus and the engineered alpha virus replicon particles derived from VEE (VRP) have a pronounced tropism for DCs and lymphocytes in vivo and in vitro (Davis et al., *J. Virol.* 70:3781-3787, 1996; MacDonald and Johnston, *J. Virol.* 74:914-922, 2000, each of which is incorporated herein by reference). VEE is a positive strand RNA virus that can cause zoonotic human disease characterized by an undifferentiated febrile illness, which can also include initial lymphopenia. In rodents and large animals, the infection by VEE can be rapidly fatal and is similarly associated with an early lymphopenia, which may be mediated by the tropism of VEE for cells of the immune system and the resultant cytopathic effect. VEE and VRP transfect a subset of human DCs of the immature phenotype. The alpha virus replicon vector system derived from VEE constitutes a replication deficient viral vector devoid of coding sequences for structural genes with coding sequences for target antigens (Pushko et al., *Virology* 239:389-401, 1997, which is incorporate herein by reference). The VRPs are constructed by co-electroporation of the VRP RNA and two separate helper RNAs encoding the required structural genes for permissive encapsulation of the VRP RNA. The resultant VRPs demonstrate an identical cellular tropism as VEE in the absence of particular attenuating mutations (Davis et al., *Virology* 212:102-110, 1995, which is incorporated herein by reference). The positive strand RNA nature of the genome of both VEE and the VRP results in rapid and robust protein production. In the case of the VRP, the target antigen is similarly expressed at high levels. Furthermore, at least in the case of a putative retroviral antigen (SIV and HIV-1), the elicited immune response includes both humoral and CTL responses (Caley et al., *Vaccine* 17:3124-3135, 1999; Davis et al., *J. Virol.* 74:371-378, 2000, each of which is incorporated herein by reference). The use of the VRP vector system allows for in vivo targeting of antigen expression in the most potent antigen presenting cells and the potential for augmenting a Th1/CTL-biased immune response to selected TAAs.

The present invention provides recombinant polynucleotides encoding a recombinant Her2/neu target antigen. Such recombinant polynucleotides are useful for genetic vaccination strategies, and the recombinant Her2/neu target antigen polypeptides are useful for polypeptide vaccination strategies. As used herein, the term "genetic vaccination" refers to the use of a nucleic acid sequence, which encodes an antigen, to stimulate an immune response, wherein expression of the encoded antigen leads to stimulation of the immune response. In comparison, the term "polypeptide vaccination" is used herein to refer to the use of a polypeptide antigen to stimulate an immune response. As disclosed herein, a genetic or polypeptide vaccination can be performed by administering a recombinant polynucleotide or polypeptide directly to an individual, or by contacting the recombinant polynucleotide or polypeptide with cells in culture, which either can be administered to the subject to treated or can be further contacted with immunoeffector cells, which are administered to the subject.

As used herein, the term "stimulate an immune response" or "immunostimulate" refers to an activation of immunoeffector cells as normally occurs upon contact of such cells with an antigen. As used herein, the term "immunoeffector cells" refers to cells that are directly involved in generating or effecting an immune response, including B lymphocytes (B cells), T cells, including CTLs and Th cells, and antigen presenting cells (APCs) such as dendritic cells, mononuclear phagocytic cells, macrophages, including Langerhans cells and, in humans, venular endothelial cells (and B cells). Stimulation of immunoeffector cells can be identified using well known immunologic methods, which are selected based on the particular immunoeffector cells that are to be stimulated. For example, stimulation of a T cell response can be identified by detecting a delayed-type hypersensitivity response in a subject, which is predictive of T cell immunity due to Her2/neu peptide immunization (see Disis et al., supra, 2000), or by detecting increased and specific CTL activity using a cell based assay (see Abbas et al., supra, 1995). Immunostimulation of B cells can be identified, if desired, by detecting the conversion of a stimulated B cell to a plasma cell, or by detecting expression (or increased expression) of a particular antibody (see, for example, Harlow and Lane, "Antibodies: A laboratory manual (Cold Spring Harbor Laboratory Press 1989)).

A recombinant polynucleotide of the invention encodes a Her2/neu target antigen, and includes at least a first nucleotide sequence, which encodes a Her2/neu target antigen having an amino acid sequence corresponding to about amino acid residues 634 to 683 operatively linked to amino acid residues 1035 to 1255 of SEQ ID NO:1 (see SEQ ID NOS:9 and 10), or to about amino acid residues 635 to 685 operatively linked to amino acid residues 1037 to 1257 of SEQ ID NO:2 (see SEQ ID NOS:3 and 4). As used herein, the term "about," when used in reference to amino acid residues of a polypeptide such as SEQ ID NO:1, means the specified amino acid residues or an amino acid sequence containing one to eight additional contiguous amino acid residues of the specified sequence, or one to eight fewer amino acid residues than the specified residues. In addition, a recombinant polynucleotide of the invention encodes a Her2/neu target antigen, and includes at least a first nucleotide sequence, which encodes a Her2/neu target antigen consisting of an amino acid sequence corresponding to amino acid residues 606 to 683 operatively linked to amino acid residues 1035 to 1255 of SEQ ID NO:1, or corresponding to amino acid residues 608 to 685 operatively linked to amino acid residues 1037 to 1257 of SEQ ID NO:2. As such, the recombinant polynucleotides, and encoded polypeptides, are distinguishable from previously described Her2/neu target antigens (see Internatl. Publ. No. WO 98/06863, which is incorporated herein by reference).

As used herein, the term "corresponding," when used in reference to a specified amino acid sequence, means an amino acid sequence of a Her2/neu homolog, which, when aligned with SEQ ID NO:1 (Entrez Protein Accession No. P04626, which is incorporated herein by reference) or SEQ ID NO:2 (Entrez Protein Accession No. P06494, which is incorporated herein by reference; see, also Entrez Protein Accession No. NP004439, which substantially encodes SEQ ID NO:2, including a few additional amino acid residues before the initial methionine of SEQ ID NO:2, but otherwise is identical), encompasses the same portion of the Her2/neu protein as the specified amino acids. As shown in FIG. 1, the amino acid sequences of human Her2/neu (SEQ ID NO:1) and rat Her2/neu (SEQ ID NO:2) are aligned, and, for example, amino acid residues 634 to 683 and 1035 to 1255 of SEQ ID NO:1 are indicated by underlining. In view of this disclosure, it will be recognized that an amino acid sequence of any other Her2/neu protein, including other mammalian Her2/neu homologs, that correspond to those shown in FIG. 1 similarly can be used to construct a Her2/neu target antigen of the invention. In general, a "corresponding" amino acid sequence is at least about 60% identical to a reference sequence (e.g., amino acid residues 635 to 685 SEQ ID NO:2), generally at least about 70% identical, and can be 80% identical, or 90% identical, or more. For example, amino acid residues 634 to 683 of SEQ ID NO:1 (human Her2/neu) are about 72% identical (35/49 residues) to the corresponding sequence of rat Her2/neu (amino acid residues 635 to 685 of SEQ ID NO:2; the exemplified proximal rat Her2/neu target sequence also contains additional amino acid residue 635 (serine) as compared to the corresponding exemplified portion of the proximal human Her2/neu target sequence; see underlining in FIG. 1A; see, also, SEQ ID NO:5). It should be recognized that an amino acid residue of a Her2/neu target antigen can be a modified amino acid, for example, a D-amino acid, which, for purposes of identifying a "corresponding" amino acid sequence, is considered to be identical to the unmodified amino acid (e.g., to an L-amino acid).

Recombinant polynucleotides of the invention are exemplified by polynucleotides encoding the amino acid sequences set forth in SEQ ID NO:4 and SEQ ID NO:10, and by polynucleotides having the nucleotide sequences set forth in SEQ ID NO:4 and SEQ ID NO:9, respectively. As shown in FIGS. 6A and 6B, an exemplified Her2/neu target antigen includes two peptide portions of rat Her2/neu (i.e., amino acid residues 635 to 685 and 1037 to 1257 of SEQ ID NO:2; see SEQ ID NO:4; see, also, SEQ ID NOS:5 and 7), which are operatively linked through a serine residue (underlined; see, also, SEQ ID NO:4), which is encoded by a portion of the BspE1 restriction endonuclease recognition site (single underline; see, also, SEQ ID NO:3) that was engineered into the polynucleotides comprising the encoding recombinant polynucleotide. Similarly, FIGS. 7A and 7B show corresponding nucleotide (SEQ ID NOS:12 and 14) and amino acid sequences (SEQ D NOS:11 and 13) of human Her2/neu useful for preparing a target antigen of the invention. In addition, the exemplified recombinant Her2/neu target antigens contain additional N-terminal methionine and alanine residues, which were included in the encoding recombinant polynucleotide to facilitate expression and to maintain the reading frame (see SEQ ID NOS:4 and 10). As such, it should be recognized that a recombinant Her2/neu target antigen can contain amino acid residues in addition to those specified.

Accordingly, a recombinant polynucleotide of the invention can further include, in addition to the Her2/neu target antigen coding sequence, a second nucleotide sequence, which is operatively linked to the sequence encoding the target antigen. As used herein, the term "operatively linked" means that a first and second (or more) nucleotide sequence are joined together such that each maintains all or a relevant part of its function. For example, where a first nucleotide sequence encodes a Her2/neu target antigen and a second nucleotide sequence includes a transcriptional promoter, the two sequences, when operatively linked, function such that the promoter can direct transcription of the coding sequence such that a transcribed mRNA can be translated. Similarly, when a first and second nucleotide each encode a polypeptide, the two sequences, when operatively linked, can encode all or a portion of each polypeptide, as desired, and can encode a fusion polypeptide including the two polypeptides, if desired. The term "operatively linked" also is used herein to refer to two or more peptides or polypeptides that are joined together such that they form a single recombinant polypeptide or fusion protein. For convenience of discussion, the term "recombinant polypeptide" is used herein to refer to a Her2/neu target antigen of the invention, which comprises a proximal and distal portion of a Her2/neu polypeptide, whereas the term "fusion protein" is used to refer to two or more other polypeptide components that are expressed as a single polypeptide or to a recombinant polypeptide of the invention operatively linked to one or more other peptides or polypeptides.

A nucleotide sequence operatively linked to the recombinant polynucleotide encoding the Her2/neu target antigen can include an expression regulatory element or can encode a heterologous amino acid sequence, for example, a polypeptide. As used herein, the term "expression regulatory element" refers to a nucleotide sequence that acts in cis to regulate the level of transcription of an operatively linked polydeoxyribonucleotide or to regulate the level of translation of polyribonucleotide (i.e., a transcriptional or translational regulatory element, respectively). Thus, an expression regulatory sequence can be a promoter, enhancer, silencer, insulator, transcription terminator, start codon (ATG), splicing signal for intron excision and maintenance of the correct reading frame, STOP codon, ribosome binding site such as an internal ribosome entry site, or the like.

A transcriptional regulatory element can be a constitutively active regulatory element or can be an inducible regulatory element, including an inducible regulatory element that is inactive in the absence of an inducing agent, or an element that is active at a basal level and is induced to a higher level in the presence of the inducing agent. In addition, the transcriptional regulatory element can be a tissue-specific regulatory element, which is active in only one or a few specific cell types, or can be a developmental stage specific regulatory element, which is active only during a certain stage of development, including in a pathologic state having the characteristics of a particular stage of development, for example, a cancer.

A transcriptional regulatory element can be a viral transcriptional regulatory element, including, for example, a cytomegalovirus promoter, an SV40 promoter or enhancer, a retrovirus U3 enhancer such as an RSV U3 enhancer, or the like. A transcriptional regulatory element also can be a transcriptional regulatory element of a eukaryotic gene, including, for example, a metallothionein promoter, which is constitutively expressed in most cell types and also is inducible; a myoD promoter, which is a tissue specific promoter that is active in differentiating or differentiated muscle cells; a lck promoter, which is a tissue specific promoter active in T cells; a myelin basic protein promoter, which is active in myelinating glial cells; a nestin promoter, which is active in neural stem cells; a dopamine β-hydroxylase or preproenkephalin promoter, which is active in particular neuronal cells; or a chemokine promoter such as a fragment of the RANTES promoter (Internatl. Publ. No. WO 98/06863). In addition, the transcriptional regulatory element can be an individual enhancer element from a eukaryotic gene, and can be present as a single copy or as multiple linked copies, or can be combined with one or more other elements present as a single copy or as multiple linked copies. Examples of such individual elements include an AP1 binding site, an Sp1 binding site, an NF κB binding site, a serum response factor binding site, a hypoxia inducing factor binding site, a cAMP responsive element, and a phosphoglycerate kinase 1 (PGK1) enhancer.

As used herein, the term "inducible," when used in reference to a transcriptional regulatory element, means a nucleotide sequence that, when present in a cell exposed to an inducing agent, effects an increased level of transcription of an operatively linked expressible polynucleotide as compared to the level of transcription, if any, in the absence of an inducing agent. The term "inducing agent" is used to refer to a chemical, biological or physical agent that effects transcription from an inducible transcriptional regulatory element. In response to exposure to an inducing agent, transcription from the element generally is initiated de novo or is increased above a basal or constitutive level of expression. An inducing agent can be, for example, a stress condition to which a cell is exposed, for example, a heat or cold shock, a toxic agent such as a heavy metal ion, or a lack of a nutrient, hormone, growth factor, or the like; or can be exposure to a molecule that affects the growth or differentiation state of a cell such as a hormone or a growth factor.

A nucleotide sequence operatively linked to a recombinant polynucleotide of the invention also can encode an amino acid sequence that is heterologous to the Her2/neu sequence. The heterologous amino acid sequence can be a peptide, for example, a cell compartmentalization domain, which can facilitate localization of the Her2/neu target antigen to a specific compartment of a cell, for example, to the cytosol, nucleus, plasma membrane, endoplasmic reticulum, mitochondrial membrane or matrix, chloroplast membrane or lumen, medial trans-Golgi cisternae, or a lysosome or endosome; a membrane translocating peptide, which can facilitate transport of a Her2/neu target antigen across a cell membrane and into an intact cell; or a secretory peptide, which can facilitate secretion of a Her2/neu target antigen out of a cell (see, for example, Hancock et al., *EMBO J.* 10:4033-4039, 1991; Buss et al., *Mol. Cell. Biol.* 8:3960-3963, 1988; U.S. Pat. No. 5,776,689, each of which is incorporated herein by reference).

A heterologous amino acid sequence also can be a peptide that acts as a tag for detecting the presence of a fusion protein containing the Her2/neu target antigen. Peptide tags, which are well known and can be conveniently synthesized or expressed from an encoding polynucleotide, include, for example, a His-6 tag, which can be detected using a divalent cation such as nickel ion or cobalt ion; a FLAG epitope, which can be detected using an anti-FLAG antibody (see, for example, Hopp et al., *BioTechnology* 6:1204 (1988); U.S. Pat. No. 5,011,912, each of which is incorporated herein by reference); a c-myc epitope, which can be detected using an antibody specific for the epitope; biotin, which can be detected using streptavidin or avidin; and glutathione S-transferase, which can be detected using glutathione. Such tags can provide the additional advantage that they can facilitate isolation of the operatively linked Her2/neu target antigen.

A heterologous amino acid sequence operatively linked to a Her2/neu target antigen also can be an immunostimulatory polypeptide, which can further stimulate an immune response induced by the Her2/neu target antigen. Immunostimulatory polypeptides include, for example, the B7 co-stimulatory molecules, and cytokines such as an interleukin, an interferon, or GM-CSF. The heterologous amino acid sequence also can be any polypeptide that can contribute to the health or well being of a subject or that constitutes part of a treatment protocol of the subject, including, for example, a polypeptide hormone or hormone analog, a chemokine or other cell or tissue growth factor.

The present invention also relates to a vector, which contains a recombinant polynucleotide of the invention, which encodes a Her2/neu target antigen. The vector can be a cloning vector, which can be useful where it is desired to manipulate the recombinant polynucleotide, for example, by operatively linking a nucleotide sequence encoding a polypeptide of interest, or can be an expression vector, which generally contains a promoter sequence and can contain a poly-A recognition sequence, a ribosome recognition site or internal ribosome entry site, or other regulatory element such as an enhancer. In addition, a vector generally contains elements required for replication in a prokaryotic or eukaryotic host system or both. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, Goeddel, ed. (Academic Press, Inc., 1990); Jolly, *Canc. Gene Ther.* 1:51-64, 1994; Flotte, *J. Bioenerg. Biomemb.* 25:37-42, 1993; Kirshenbaum et al., *J. Clin. Invest.* 92:381-387, 1993; each of which is incorporated herein by reference).

A vector useful for containing a recombinant polynucleotide of the invention can be a plasmid vector or a viral vector. Methods of making a viral vector containing a recombinant polynucleotide are known in the art (see Larrick and Burck,

*Gene Therapy, Applications of Molecular Biology* (Elsevier, NY, 1991), which is incorporated herein by reference). If desired, the viral vector can be replication defective, in which case an appropriate helper cell line is required to produce viral particles containing the viral vector. A viral vector can be based, for example, on an alphavirus, a retrovirus, an adenovirus, an adeno-associated virus, a vaccinia virus, or the like.

A retrovirus vector, for example, can be made by a retrovirus producer cell, which, in turn, can be made by transfecting a plasmid, such as pLXSN into a retrovirus packaging cell line such as PA317 (see, Miller and Rosman, *BioTechniques* 7:980-990, 1989; Miller and Buttimore, *Mol. Cell. Biol.* 6:2895-2902, 1986, each of which is incorporated herein by reference). A cell transfected with pLXSN is resistant to neomycin and, therefore, a stably transfected colony can be selected in a culture media supplemented with active neomycin, for example G418. Neomycin resistant cell lines can be identified by screening them for the production of replication defective murine leukemia retroviruses using known methods (see, Cepko, In *Current Protocols in Molecular Biology*, Suppl. 17, pp. 9.11.5-9.11.12, (Wiley-Interscience, NY 1992), which is incorporated herein by reference).

A retrovirus vector can be made by inserting a recombinant polynucleotide of the invention into the selected vector plasmid. The recombinant polynucleotide can be operatively linked to expression control sequences prior to introduction into the vector plasmid, or the vector can contain the required regulatory elements, to which the recombinant polynucleotide is operatively linked upon insertion into the vector plasmid. The retrovirus vector then is transfected into an appropriate helper cell line such that vectors containing the recombinant polynucleotide are produced. Additional methods of making retrovirus vectors are known in the art (see, U.S. Pat. Nos. 5,399,347; 5,532,220; 5,240,846; Ram et al., *Cancer Res.* 53:83-88, 1993, each of which is incorporated herein by reference).

In addition to retroviral vectors, other viral vectors can be made and used for purposes of the present invention. For example, methods of making recombinant adenoviral vectors are well known (see, Karlsson et al., *EMBO J.* 5:2377-2385, 1986; Kleinerman et al., *Cancer Res.* 55:2831-2836, 1995; Hamada et al., *Gynecol. Oncol.*, 63:219-227, 1996; Nabel et al., *Science,* 249:1285-1288, 1990; Berkner, *Bio Techniques* 6:616-629, 1989, each of which is incorporated herein by reference). Other recombinant viral vectors, such as adeno-associated virus vector, herpesvirus vectors, and vaccinia virus vectors are well known in the art (see Culver, *Gene Therapy, A Handbook for Physicians* (Mary Ann Liebert, Inc., NY 1994), which is incorporated herein by reference; see, also, Larrick and Burck, supra, 1991).

An alphavirus vector such as a Venezuelan equine encephalitis virus (VEE) vector (AlphaVax, Inc.; Durham N.C.; see U.S. Pat. Nos. 5,792,462, and 6,008,035, each of which is incorporated herein by reference) can be particularly useful where the recombinant polynucleotide of the invention is to be used for administration to a subject in order to stimulate an immune response. Alphavirus VEE vectors have been used to successfully vaccinate rodents and non-human primates against influenza, Lassa fever, Ebola virus, Marburg virus, and botulinum toxin (U.S. Pat. No. 5,643,576; Hevey et al., *Virology* 251:28-37, 1998, each of which is incorporated herein by reference; see, also, Pushko et al., supra, 1997). VEE vectors have particular advantages over other vaccine technologies, including they direct high antigen expression levels and show sustained efficacy over multiple simultaneous or sequential innoculations of the vector. In addition, VEE vectors are not likely to be subject to an existing vector-specific immune response, particularly in a human patient.

The present invention also provides a cell containing a recombinant polynucleotide or a vector of the invention. Such a cell can be a prokaryotic cell or eukaryotic cell, particularly a mammalian cell. Where the cell contains a vector of the invention, the cell can be host cell that is useful, for example, for propagating the vector, including the recombinant polynucleotide of the invention, or for expressing an encoded Her2/neu target antigen. Where the vector is a viral vector plasmid, the cell also can be a helper cell, which provides in trans any factors necessary for replication and packaging of viral particles containing the viral vector. A cell containing a recombinant polynucleotide of the invention also can be an immunoeffector cell, for example, an APC such as a dendritic cell, in which the encoded Her2/neu target antigen can be expressed and processed for presentation to T cells, or can be a cell from which the encoded Her2/neu target antigen is secreted, such a cell being useful for stimulating an immunoeffector cell such as an APC by providing the APC with the target antigen.

The present invention also relates to a recombinant polypeptide, which includes a Her2/neu target antigen having an amino acid sequence corresponding to about amino acid residues 634 to 683 operatively linked to amino acid residues about 1035 to 1255 of SEQ ID NO:1, or to about amino acid residues 635 to 685 operatively linked to about amino acid residues 1037 to 1257 of SEQ ID NO:2, or which includes a Her2/neu target antigen consisting of an amino acid sequence corresponding to amino acid residues 606 to 683 operatively linked to amino acid residues 1035 to 1255 of SEQ ID NO:1, or to amino acid residues 608 to 685 operatively linked to amino acid residues 1037 to 1257 of SEQ ID NO:2. A polypeptide of the invention is exemplified by a Her2/neu target antigen having an amino acid sequence as set forth in SEQ ID NO:4, or an amino acid sequence corresponding thereto, for example, as set forth in SEQ ID NO:10. A recombinant polypeptide of the invention can be expressed from a recombinant polynucleotide of the invention or can be chemically synthesized. As such, the Her2/neu target antigen can contain, for example, one or more D-amino acids in place of a corresponding L-amino acid; or can contain one or more amino acid analogs, for example, an amino acid that has been derivatized or otherwise modified at its reactive side chain. Similarly, one or more peptide bonds in the Her2/neu target antigen can be modified, or a reactive group at the amino terminus or the carboxy terminus or both can be modified. Such modified Her2/neu target antigens can have improved stability to a protease, an oxidizing agent or other reactive material the polypeptide may encounter in a biological environment such as a tissue culture medium or in a living subject and, therefore, can be particularly useful in performing a method of the invention.

The present invention also provides a method for expressing a Her2/neu target antigen in a cell. Such a method can be performed, for example, by contacting the cell with the recombinant polynucleotide, for example, a nucleic acid molecule comprising SEQ ID NO:4 or SEQ ID NO:9 or encoding SEQ ID NO:4 or SEQ ID NO:10, under conditions that allow expression of the encoded Her2/neu target antigen by the cell. The contacting is performed under conditions such that the recombinant polynucleotide is introduced into the cell, wherein that the encoded Her2/neu target antigen can be expressed.

Methods for introducing a polynucleotide into a cell are well known in the art and include, for example, transfection, lipofection, microinjection, electroporation, ballistic methods, and, with viral vectors, infection; and can include the use of liposomes, microemulsions or the like, which can facilitate introduction of the polynucleotide into the cell and can protect the polynucleotide from degradation prior to its introduction into the cell (see, for example, Sambrook et al., *Molecular Cloning: A laboratory manual* (Cold Spring Harbor Laboratory Press 1989); Ausubel et al., *Current Protocols in Molecular Biology* (John Wiley & Sons, Baltimore Md. 1987, and supplements), each of which is incorporated herein by reference). For example, the recombinant polynucleotide, which can be in a vector, can be incorporated into a liposome, which can be made target cell specific, if desired, by incorporating, for example, a lipid-conjugated antibody or other receptor or ligand specific for a particular target cell (see, for example, Nabel et al., *Proc. Natl. Acad. Sci. USA*, 90:11307-11311 (1993); Holmberg et al., *J. Liposome Res.*, 1:393-406 (1990), each which is incorporated herein by reference). The selection of a particular method for introducing the recombinant polynucleotide into a cell will depend, for example, on the cell into which the polynucleotide is to be introduced, as well as whether the cell is isolated in culture, or is in situ in a subject.

Introduction of a polynucleotide into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference). Moreover, viruses are very specialized and can be selected as vectors based on an ability to infect one or a few specific cell types. Thus, their natural specificity can be used to target the recombinant polynucleotide to specific cell types. As such, a vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events. As described above, alphavirus VEE vectors have been used to successfully vaccinate rodents and non-human primates against various infective viruses and toxins and, therefore, can be particularly useful for practicing the methods of the invention.

The cell to be contacted can be any cell in which the Her2/neu target antigen can be expressed, including prokaryotic and eukaryotic cells, and particularly mammalian cells. The cell can be contacted with the recombinant polynucleotide in culture, in which case the cell can be one that that has been established for passage in tissue culture. Where the cells are adapted to tissue culture, the cells expressing a Her2/neu target antigen can comprise a panel of such cells, for example, a panel of dendritic cells having different but known haplotypes. Such panels of cells can be useful as a convenient source from which a clinician can select a particular dendritic cells for administration to a patient in whom it is desired to stimulate an immune response against cells expressing Her2/neu. In addition, the cell can be one or a population of cells that has been removed from the subject and is contacted ex vivo, or the contacting can be performed in vivo. Where the contacting is performed in vivo, the recombinant polynucleotide can be administered to the site of cell or to a site to which the cell can migrate, or can be administered systemically such that it can circulate to the cells in which the Her2/neu target antigen is expressed. In addition, the recombinant polynucleotide can, but need not, be contained in a vector, which can be a viral vector. In general, the recombinant polynucleotide is operatively linked to expression regulatory elements required for transcription and translation, although such elements can be a component of a vector containing the recombinant polynucleotide.

The present invention also provides a method of isolating a Her2/neu target antigen from a cell expressing the target antigen. Such a method can be performed by contacting the cell with a recombinant polynucleotide of the invention under conditions that allow expression of the encoded Her2/neu target antigen by the cell, and isolating the expressed Her2/neu target antigen from the cell. The Her2/neu target antigen can be isolated from the cell using any convenient method, including, for example, by an affinity chromatography method such as immunoaffinity chromatography, a gel filtration chromatography method or by gel electrophoresis of a protein extract prepared from cells expressing the Her2/neu target antigen (see, for example, Deutscher, *Guide to Protein Purification*, Academic Press, Inc., 1990, which is incorporated herein by reference). An affinity chromatography method, for example, can be based on the binding of a peptide operatively linked to the Her2/neu target antigen, for example, a polyhistidine tag peptide, which can be bound by a nickel ion chelate. If desired, a polypeptide such as a peptide tag that is operatively linked to a Her2/neu target antigen of the invention can further contain a cleavage site positioned between the target antigen and the peptide, for example, a protease or chemical cleavage site, which is not also present in the Her2/neu target antigen, such that, upon isolation of the fusion protein, the Her2/neu target antigen can be released from the operatively linked peptide or polypeptide. Accordingly, the present invention also provides an isolated Her2/neu target antigen obtained by such a method.

The present invention provides a method of obtaining a cell that is genetically modified to express a Her2/target antigen by contacting a cell with a recombinant polynucleotide of the invention under conditions that allow expression of the encoded Her2/neu target antigen by the cell, and isolating a cell expressing the Her2/neu target antigen. Such cells can be isolated, for example, by including the recombinant polypeptide in a vector containing a selectable marker such as an antibiotic resistance gene, or by operatively linking a nucleotide sequence encoding a selectable marker to the recombinant polypeptide, such that cells expressing the marker and, therefore, the Her2/neu target antigen, can be selected. Cells selected by such a method can further be cloned, for example, by performing a limiting dilution of the cells. Accordingly, the present invention further provides an isolated cell, which expresses the Her2/neu target antigen, obtained by such a method.

The present invention also provides methods of stimulating an immune response in a subject against cells that express Her2/neu. The cells that express Her2/neu can be cancer cells or any other cells that express Her2/neu, particularly cells involved in a pathologic condition. The disclosed methods are particularly useful for stimulating an immune response against cells that are involved in a pathologic condition and overexpress Her2/neu as compared to corresponding cells that are not involved in the pathologic condition. For example, the cells can be cancer cells that overexpress Her2/neu as compared to the level of Her2/neu expressed by normal cell counterparts to the cancer cells. In one embodiment, a method of stimulating an immune response in a subject against cancer cells that express Her2/neu is performed by contacting cells with a recombinant polynucleotide of the invention under conditions that allow expression from the recombinant polynucleotide of the Her2/neu target antigen in the cells. The cells that are contacted with the recombinant polypeptide can be autologous or allogeneic with respect to the subject to be treated, and, where autologous, can be contacted ex vivo or in vivo. In addition, the cells that are contacted with the recombinant polynucleotide can be antigen presenting cells (APCs) or can be cells that can express and secrete the Her2/neu target antigen such that it can be taken up and processed by an APC.

A cell to be contacted with a recombinant polynucleotide of the invention can be contacted in a culture medium, generally a tissue culture medium or other physiologically acceptable medium that is conducive to survival of the cells at least for the time required to introduce the recombinant polynucleotide into the cell, for example, a physiological saline solution. Where the cell that is contacted with the recombinant polynucleotide is an APC, a method of stimulating an immune response is performed by administering the APCs, which are expressing the Her2/neu target antigen, to the subject, such that the APCs can present the processed antigen to immunoeffector cells. Where the cell that is contacted with the recombinant polynucleotide is a cell other than an APC, for example, a fibroblast, the recombinant polynucleotide can further include an operatively linked nucleotide sequence encoding a secretory peptide, which allows secretion of the Her2/neu target antigen from the cell. The cell expressing (and secreting) the Her2/neu target antigen then is contacted with an APC, either in culture, or by administering the cell to the subject to be treated such that an APC in the subject can take up and process the target antigen for presentation to other immunoeffector cells, including Th cells and CTLs. Where the cells that express the Her2/neu target antigen and the APCs are contacted in culture, APCs that have endocytosed the Her2/neu target antigen, and, if desired, the cells expressing the Her2/neu target antigen are administered to the subject to be treated.

A cell to be contacted with a recombinant polynucleotide of the invention also can be contacted in vivo. The cells to be contacted in vivo can be APCs, cells other than APCs, which can secrete the Her2/neu target antigen such that APCs can endocytose and process the target antigen, or a combination of such cells. The recombinant polynucleotide, which generally is formulated as a pharmaceutical composition, can be administered to the subject as a naked DNA molecule, which can be contained in a vector, or can be formulated in a liposome or other matrix that facilitates uptake of the recombinant polynucleotide by a cell, or can be contained in a viral particle, for example, a VEE replicon particle (AlphaVax, Inc.).

In another embodiment, a method of immunostimulating immunoeffector cells against cancer cells expressing Her2/neu is performed by contacting the immunoeffector cells, particularly APCs, with a recombinant Her2/neu target antigen polypeptide. The immunoeffector cells can be any cells that can be immunostimulated due to contact with the recombinant polypeptide, particularly antigen presenting cells such as dendritic cells, B cells, and the like. The contacting can be performed on cells in culture, which can be autologous cells or allogeneic cells, or can be performed in vivo by administering the recombinant polypeptide to the subject. Where the cells are contacted in culture, the immunostimulated cells can be isolated, if desired. As such, the present invention also provides a method of isolating immunoeffector cells that have been immunostimulated due to contact with a Her2/neu target antigen, and further provides an isolated immunostimulated cell isolated by such a method.

For administration to a subject, a recombinant Her2/neu target antigen or an encoding recombinant polynucleotide generally is formulated as a pharmaceutical composition. Accordingly, the present invention provides a pharmaceutical composition, which generally contains, in addition to the recombinant polynucleotide or polypeptide of the invention, a pharmaceutically acceptable carrier, for example, an aqueous solution such as physiologically buffered saline or other solvent or vehicle such as a glycol, glycerol, an oil such as olive oil or an injectable organic esters. A pharmaceutically acceptable carrier also can include a physiologically acceptable compound that acts, for example, to stabilize the Her2/neu target antigen or encoding recombinant polynucleotide or to increase its absorption. Physiologically acceptable compounds include, for example, carbohydrates, such as glucose, sucrose or dextrans, antioxidants, such as ascorbic acid or glutathione, chelating agents, low molecular weight proteins or other stabilizers or excipients. Similarly, a cell that has been treated in culture for purposes of the practicing the methods of the invention also can be formulated in a pharmaceutical composition when the cells are to be administered to a subject.

One skilled in the art would know that the choice of a pharmaceutically acceptable carrier, including a physiologically acceptable compound, depends, for example, on whether a Her2/neu target antigen polypeptide or an encoding polynucleotide is to be administered, as well as on the route of administration of the composition. Where the pharmaceutical composition is administered as a vaccine, it generally is administered intramuscularly, intradermally, or subcutaneously. However, it also can be administered orally or parenterally such as intravenously, and can be administered by injection, intubation, or other such method known in the art.

A pharmaceutical composition of the invention also can contain a second reagent such as a diagnostic reagent, nutritional substance, toxin, or therapeutic agent, for example, a cancer chemotherapeutic agent, or an immunostimulatory agents such as a cytokine or a B7 molecule In addition, a pharmaceutical composition containing a recombinant polypeptide Her2/neu target antigen can contain an adjuvant, for example, alum, DETOX adjuvant (Ribi Immunochem Research, Inc.; Hamilton Mont.), or Freund's complete or incomplete adjuvant. The addition of an adjuvant can enhance the immunogenicity of a Her2/neu target antigen, thus decreasing the amount of target antigen required to stimulate an immune response. Adjuvants can augment the immune response by prolonging antigen persistence, enhancing co-stimulatory signals, inducing granuloma formation, stimulating lymphocyte proliferation nonspecifically, or improving apposition of a T cell and an APC.

A recombinant polynucleotide or polypeptide of the invention also can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley, et al., *Trends Biochem. Sci.*, 6:77, 1981, each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating material. Cationic liposomes, for example, also can be modified with specific receptors or ligands (Morishita et al., *J. Clin. Invest.*, 91:2580-2585, 1993, which is incorporated herein by reference). In addition, a polynucleotide agent can be introduced into a cell using, for example, adenovirus-polylysine DNA complexes (see, for example, Michael et al., *J. Biol. Chem.* 268:6866-6869, 1993, which is incorporated herein by reference).

The total amount of a pharmaceutical composition to be administered in practicing a method of the invention can be administered to a subject as a single dose, either as a bolus or by infusion over a relatively short period of time, and can be followed up with one or more booster doses over a period of time. One skilled in the art would know that the amount of the pharmaceutical composition to stimulate an immune response in a subject depends on various factors including the age and general health of the subject, as well as the route of administration and the number of treatments to be administered. In view of these factors, the skilled artisan would adjust the particular dosage as necessary. In general, the formulation of the pharmaceutical composition and the routes and frequency of administration are determined, initially, using Phase I and Phase II clinical trials.

The present invention also relates to a method of making a target antigen, which can stimulate an immune response against a protein expressed on the surface of a cancer cell. Such a method can be performed, for example, by selecting a first peptide portion of the protein, wherein the first peptide portion includes the transmembrane domain and has limited homology to proteins other than the protein expressed on the surface of the tumor cell; selecting a second peptide portion of the protein, which includes a portion of the cytoplasmic domain of the protein and has limited homology to proteins other than the protein expressed on the surface of the tumor cell; and operatively linking the first peptide portion and the second peptide portion, thereby making the target antigen. As used herein, the term "limited homology" is used relatively to indicate that a reference peptide having a defined amino acid sequence has less than about 30% sequence identity with proteins to which it is being compared. In general, the less homology a sequence of a reference peptide (i.e., a peptide portion of a protein to be used for constructing a target antigen) has with proteins that are normally expressed in a subject to which the target antigen is to be administered, the better suited the peptide is for making the target antigen. Such limited homology can be determined using readily available search algorithms, such as BLASTP and the like.

The following example is intended to illustrate but not limit the invention.

EXAMPLE 1

Her2/neu Vaccine Protects Against Tumor Growth

This example demonstrates that a vaccine based on regions of the Her2/neu protein that are not present in other proteins increase survival in a syngeneic rat tumor model.

The Her2/neu breast cancer tumor associated antigen (TAA) was selected as the prototypical target antigen for the development and evaluation of genetic vaccination strategies. The Her2/neu protein is a member of the c-erb B/epidermal growth factor receptor family and is overexpressed in approximately 35% of breast cancers (Harris et. al., Cancer of the Breast, in "CANCER: Principles & Practice of Oncology" (Devita and Rosenberg, Eds., J.B. Lippincott Co., Philadelphia Pa., 1993)). The Her2/neu protein was selected as a target antigen because immune recognition of this TAA has been reported (Disis et al., *Clin. Cancer Res.* 5:1289-1297, 1999; Tuttle et al., *Clin. Cancer Res.* 4:2015-2024, 1998, each of which is incorporated herein by reference), and because, if a robust anti-TAA immune response was generated using a genetic vaccination strategy, the critical issues of specificity of response and potential cross-reactive auto-immune phenomena could be addressed.

Two regions of the human Her2/neu molecule demonstrating the lowest degree of homology with other known normal human proteins were selected as the putative target antigen sequence for a genetic vaccination strategy. The selected regions include a 49 amino acid sequence encompassing the transmembrane domain (amino acids 634 to 683 of SEQ ID NO:1) and a 221 amino acid sequence of the intracellular domain (amino acids 1035 to 1255 of SEQ ID NO:1). When combined to form a single polypeptide, the new sequence did not have any significant homology with normal proteins when examined using a BLAST search through NCBI and a FASTA search covering SwissPro and other databases. This target sequence, which contain some of the previously identified T cell epitopes (Disis et al., supra, 1999), was selected to minimize any potential cross-reactive, autoimmune responses and to maximize the specificity of the elicited immune response. Because this sequence is predominantly intracellular and represents a truncated or partial protein sequence, it should be rapidly degraded and presented in the context of MHC class 1 and, therefore, available for CTL recognition (Rock and Goldberg, *Ann. Rev. Immunol.* 17:739-779, 1999, which is incorporated herein by reference).

The high degree of homology between human Her2/neu and rat neu sequences (Yamamoto et al., *Nature* 319:230-4, 1986, which is incorporated herein by reference) allowed for the construction of an entirely homologous sequence of rat neu for use as a putative target antigen sequence in an established rat model of mammary carcinoma. The rat mammary tumor cell line, 13762 MAT BIII (ATCC, CRL 1666), was derived from the Fisher 344 strain and represents a syngeneic tumor line (Segaloff, *Recent Prog. Horm. Res.* 22:351-379, 1966, which is incorporated herein by reference). Subcutaneous (SC) inoculation of $5\times10^4$ tumor cells results in the establishment of a tumor nodule in approximately 10 days with sufficient growth requiring euthanization of untreated animals in 5-8 days. This tumor expresses low levels of rat MHC class 1 and modest levels of rat neu as evaluated by flow cytometry. The low level expression of MHC class 1 in the tumor model recapitulates the findings in human breast cancer (Pistillo et al., *Hum. Immunol.* 61:397-407, 2000; Vitale et al., *Cancer Res.* 58:737-42, 1998, each of which is incorporated herein by reference). In view of this result, coupled with the modest overexpression of rat neu and the aggressive growth characteristics of this tumor, this model system provides a rigorous, entirely syngeneic model of breast cancer for testing immunotherapeutic strategies.

It is noted that rat neu transgenic mouse models exist, including models that use an activated and transforming mutated rat neu (Bouchard et al., *Cell* 57:931-936, 1989; Guy et al., *J. Biol. Chem.* 271:7673-7678, 1996; Muller et al., *Cell* 54:105-115, 1988, each of which is incorporated herein by reference) or that use a putative wild type rat neu, which may have undergone activating mutations, under the control of various promoters. As with most transgenic models, however, it is unclear whether expression of the transgene is regulated in a manner identical to that seen in the natural host. The Fisher 344 rat model was selected due, in part, to these concerns.

The target antigen sequence was derived from 13762 tumor mRNA using reverse transcription-PCR. The nucleotide sequence encoding the transmembrane fragment of the target antigen is shown in FIG. 6A (proximal rat Her2/neu polypeptide; SEQ ID NO:6). The amplified sequence contains an introduced BspE1 site (underlined), which was encoded by the PCR primers. FIG. 6B shows the nucleotide sequence encoding the terminal cytoplasmic fragment (SEQ ID NO:8), again with the introduced BspE1 site underlined. FIG. 6A also shows the recombinant polynucleotide (SEQ ID NO:3) and encoded Her2/neu target antigen (SEQ ID NO:5), with the additional sequences added to initiate translation and maintain reading frame double underlined and the fusion site, including an additional inserted serine residue underlined. SEQ ID NO:3 was prepared by PCR amplification of a template prepared by linking SEQ ID NOS:6 and 8 at the BspE1 site (underlined). The coding sequence of the Her2/neu antigen (SEQ ID NO:3) and the amino acid sequence (SEQ ID NO:4) of the encoded antigen are shown (FIG. 1). FIG. 2 shows the corresponding nucleotide and amino acid sequences of human Her2/neu (SEQ ID NOS:9-14).

The nucleotide sequence encoding the Her2/neu target antigen (SEQ ID NO:3) was cloned into the polynucleotide vaccine vector, pITL (Internatl. Publ. No. WO 98/06863). Purified plasmid (with or without the target antigen sequence) containing endotoxin levels less than 5 EU per mg DNA was produced (Prieto et al., BioTechniques 29:1204-1206, 2000, which is incorporated herein by reference). Animals received three separate intramuscular vaccinations of 100 μg of covalently closed circular plasmid DNA at three week intervals. Positive control animals received $1\times10^6$ irradiated (20 cGy) 13762 tumor cells in the subcutaneous space on the same schedule. A tumor challenge of $5\times10^4$ viable tumor cells was administered subcutaneously 3 weeks after completion of the vaccination regimen. Animals developing tumors were euthanized at the designated maximal tumor dimension.

Administration of the target antigen DNA vaccine resulted in a statistically significant (p=0.02; log rank analysis) delay in tumor outgrowth (FIG. 2), but no protection was observed; all animals developed tumors. The DNA vaccine regimen also resulted in a significant tumor-specific proliferative response.

Figure 3:
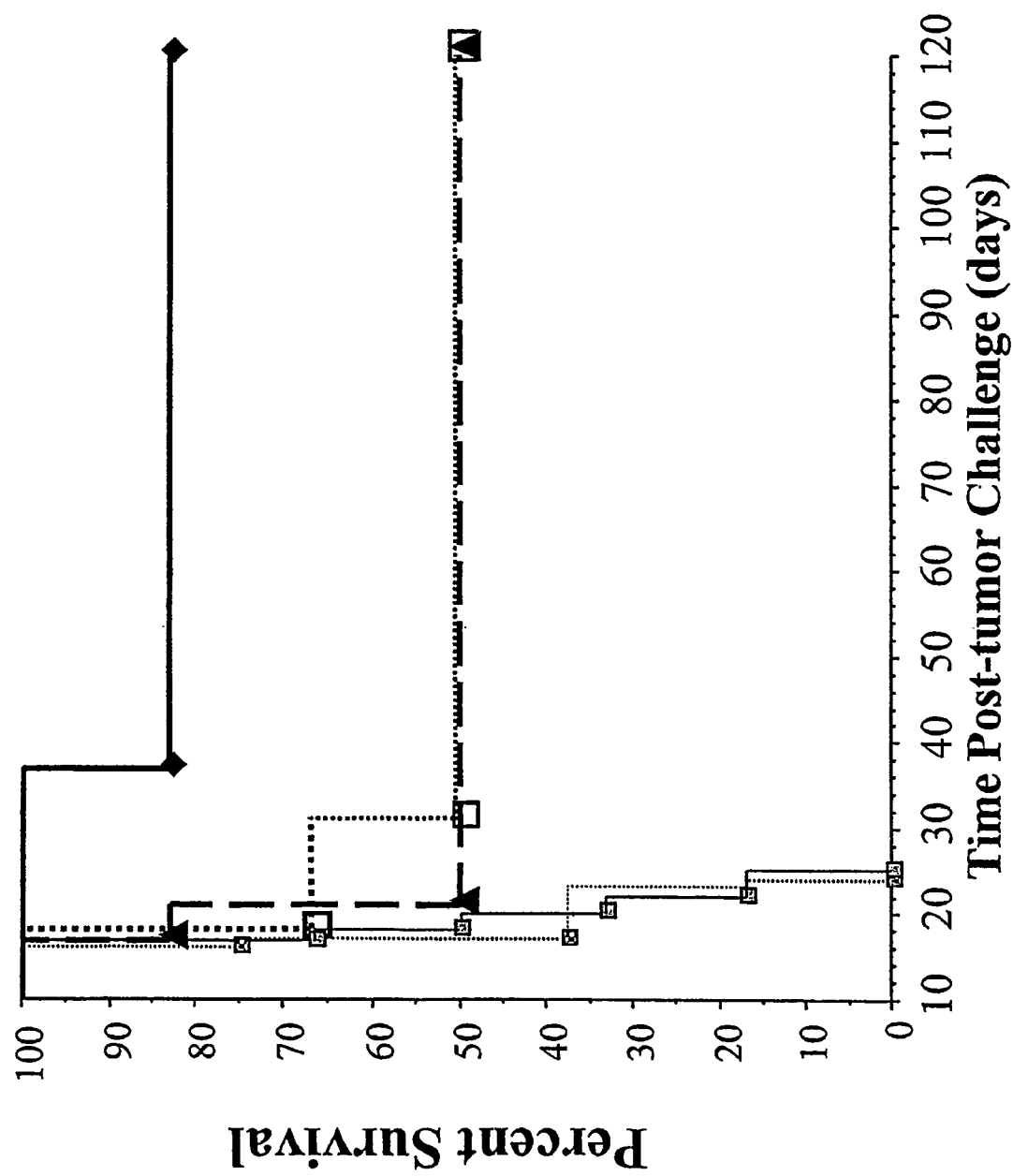
FIG. 3 compares the percent survival (ordinate) with time after tumor cell challenge (abscissa) of control Fisher 344 rats (no vaccination, open triangles) and Fisher 344 rats treated with $1\times10^6$ infectious units (ifu) of irradiated 13762 mammary carcinoma cells (closed squares), $1\times10^7$ ifu of VRP-rNeu, intramuscularly (IM; closed triangles), $1\times10^7$ ifu VRP-rNeu, subcutaneously (SC; open squares), or $1\times10^7$ ifu VRP-HA, SC (open circles; see Example 1).
Figure 4A:
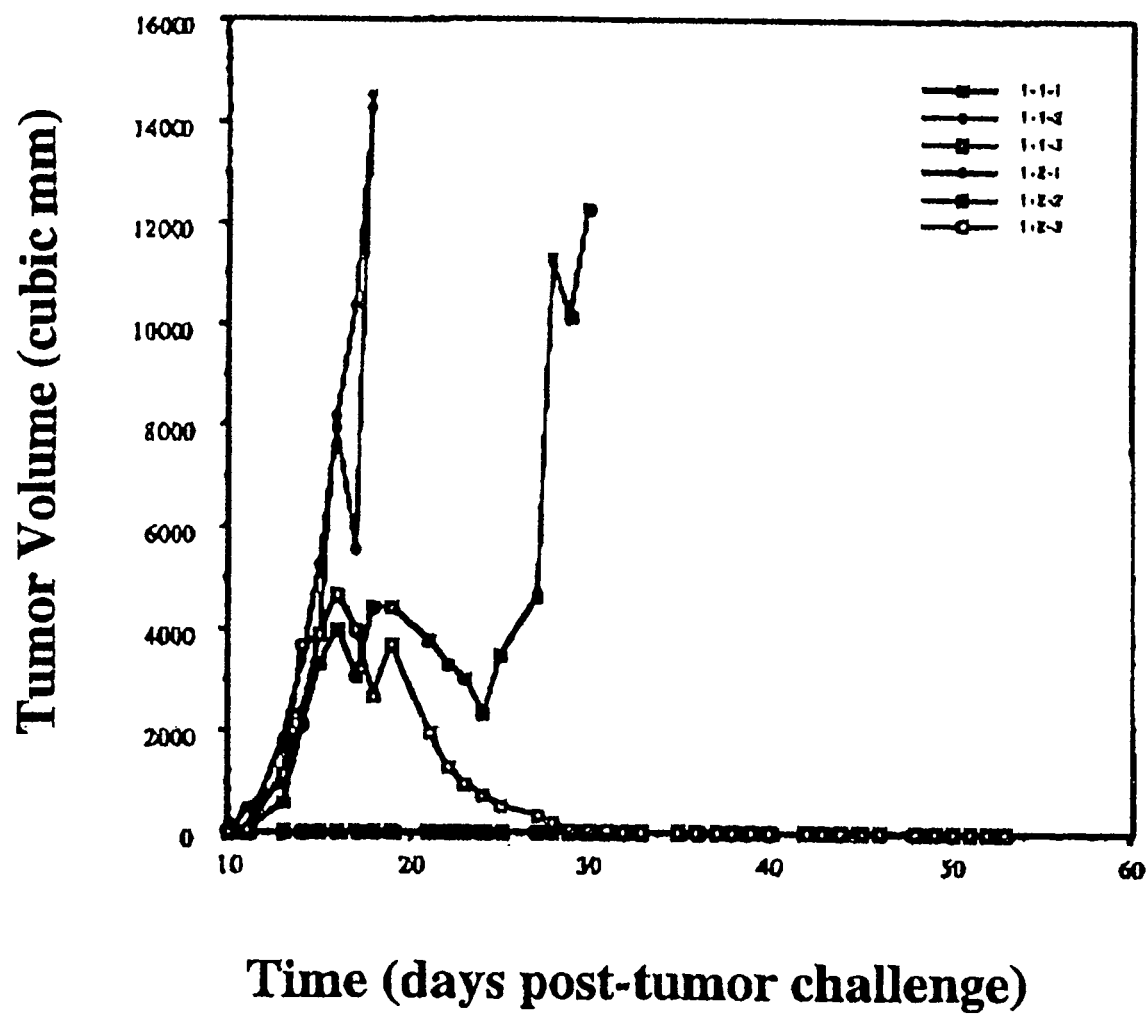
FIGS. 4A to 4C show the tumor volumes ($mm^3$; ordinate) of individual rats with time after tumor challenge (abscissa). Rats were vaccinated with $1\times10^7$ ifu VRP-rNeu, IM (FIG. 4A); $1\times10^6$ ifu VRP-rNeu, SC (FIG. 4B); or $1\times10^5$ ifu VRP-rNeu, SC (FIG. 4C).
Figure 4B:
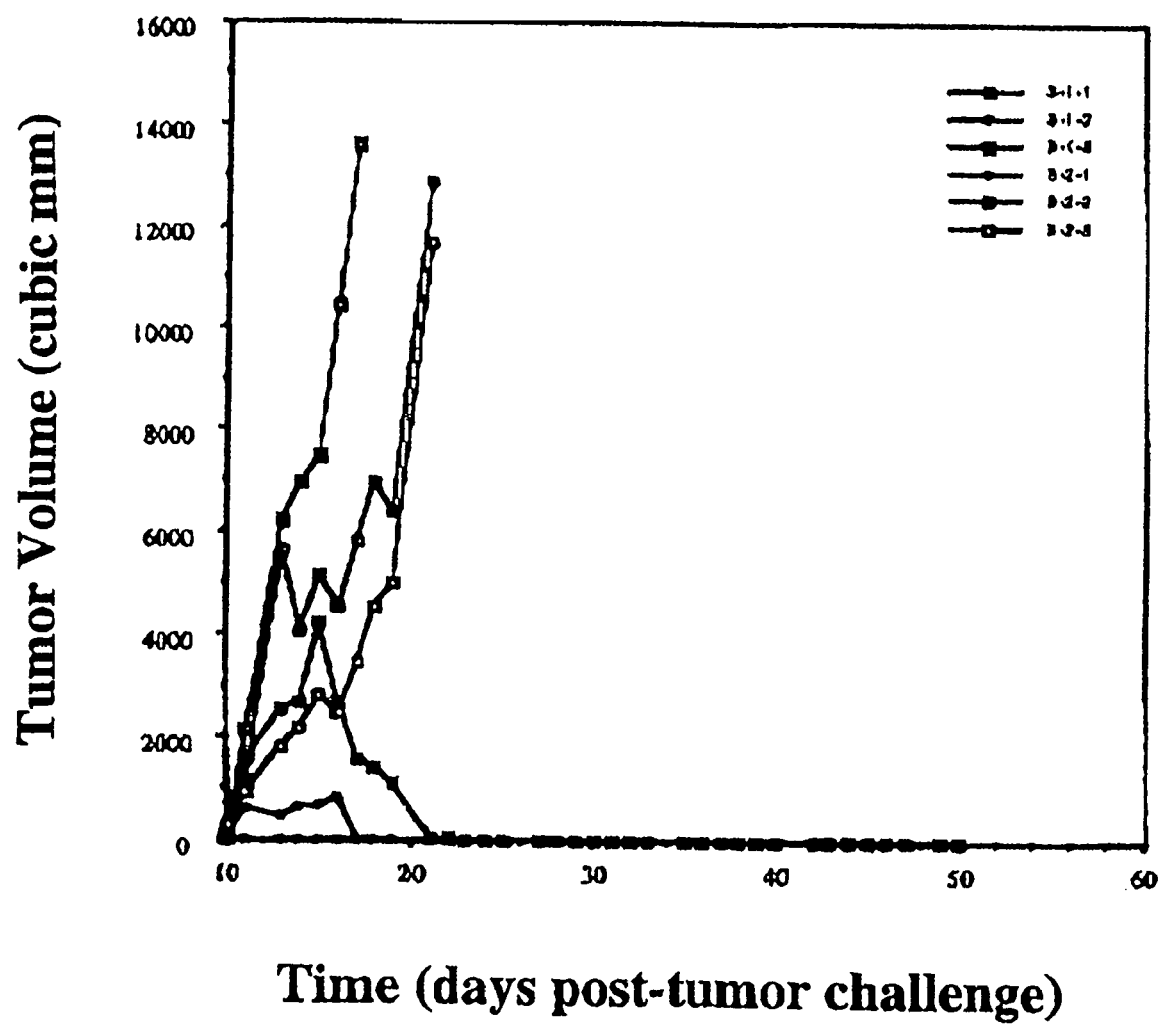
Figure 4C:
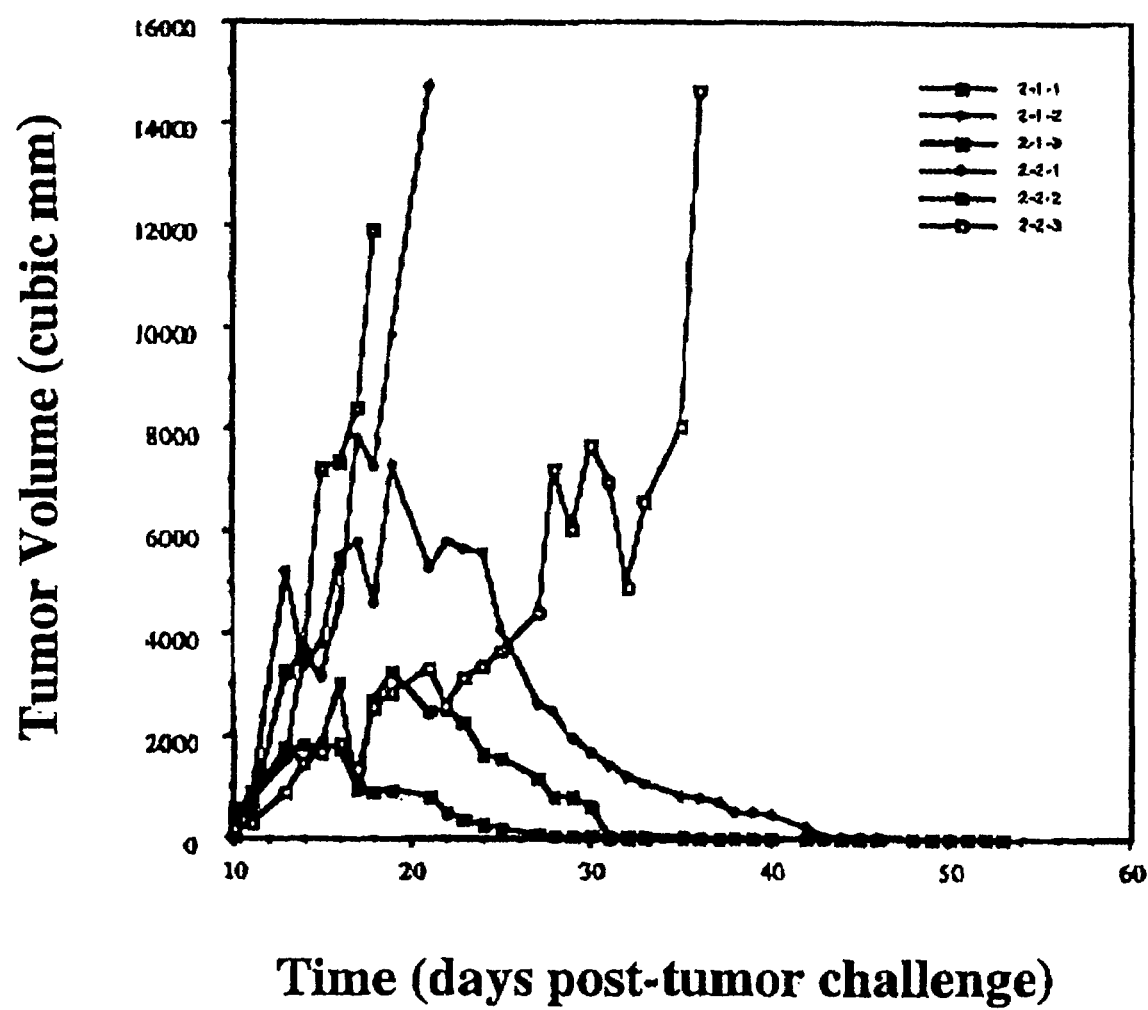

The target antigen coding sequence (SEQ ID NO:5) also was cloned into the construct for inclusion in the Venezuelan equine encephalitis virus (VEE) replicon particles (VRP; see U.S. Pat. Nos. 5,792,462, and 6,008,035); this vector was designated VRP-rNeu. VRP containing the influenza hemagglutinin antigen (VRP-HA) was used as a specificity control. Very similar results were obtained in two separate experiments. Intramuscular or subcutaneous injection of $1\times10^7$ infectious units (ifu) of VRP-rNeu, administered every three weeks for a total of three injections, resulted in approximately 50% survival without tumor after tumor challenge in excess of 120 days, (FIG. 3; see, also FIG. 4A, showing growth of tumors in individual animals receiving $1\times10^7$ ifu, intramuscularly). Lower doses ($1\times10^6$ ifu or $1\times10^5$ ifu) of VRPs also were administered subcutaneously. As shown in FIGS. 4B and 4C, tumor growth on average was delayed in an apparently dose-dependent relationship.

Figure 5:
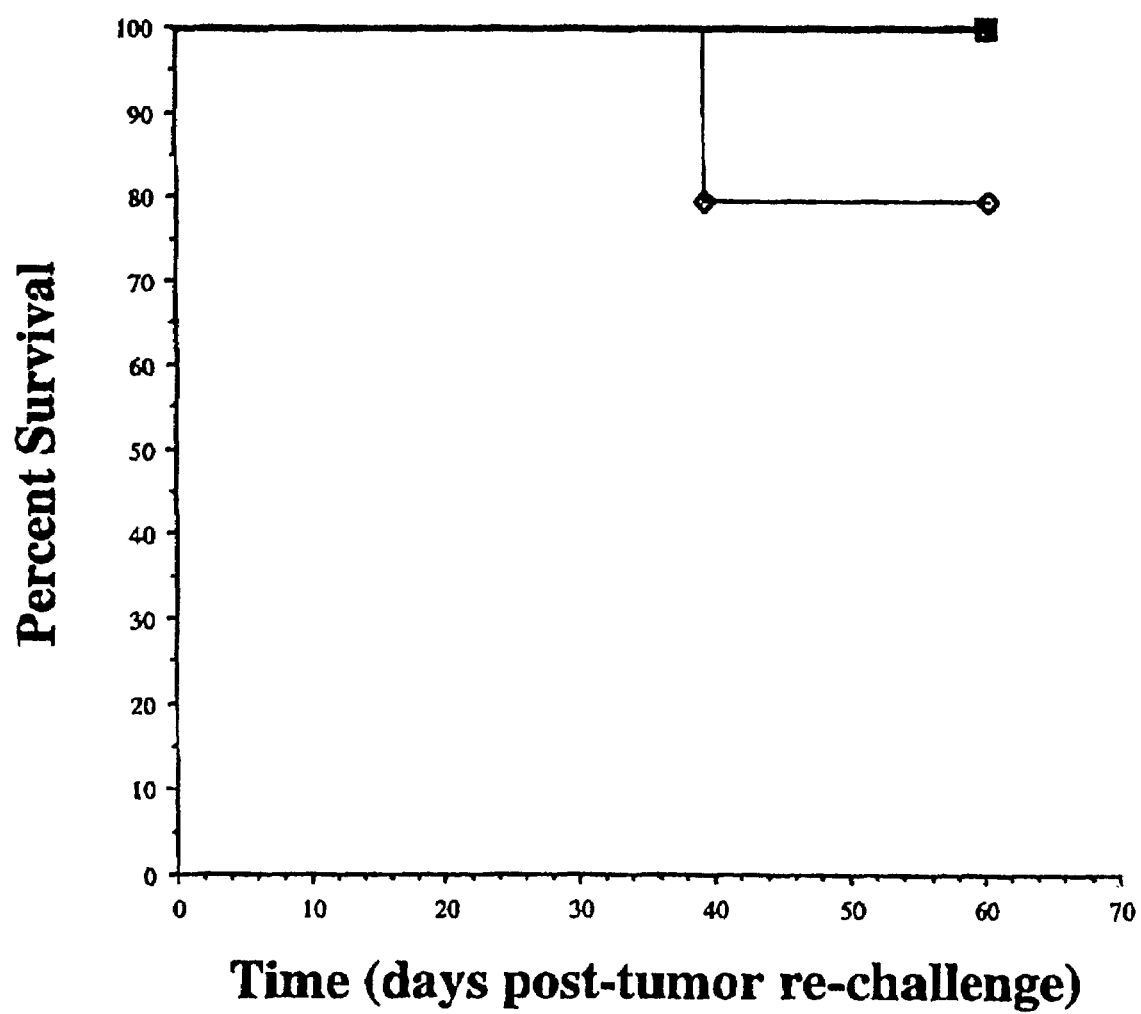
FIG. 5 shows the percent survival (ordinate) with time after tumor cell re-challenge of surviving animals (see Example 1). Initial treatments of surviving animals was $1\times10^7$ ifu VRP-rNeu, IM (closed square); $1\times10^6$ ifu VRP-rNeu, SC (closed triangle); $1\times10^5$ ifu VRP-rNeu, SC (open circle); or $1\times10^6$ irradiated 13762 cells (diamond). Note: closed triangle and open circle are included within the closed square.

Tumor-free survival was a result of both overt protection, seen only in the IM route, and in permanent regression of tumors in 25-50% of the animals. This regression suggested that there was an immunologic basis for the survival benefit. Accordingly, surviving animals were re-challenged 120 days after the initial tumor challenge with an identical dose of viable 13762 tumor cells. All vaccinated animals rejected the tumor challenge, while control animals developed tumors (FIG. 5), indicating that these animals have immunologic memory.

These results indicate that a genetic vaccine encoding the Her2/neu target shown as SEQ ID NO:4 reduced or inhibited breast cancer cell growth in a syngeneic animal model, and that the effectiveness of the vaccination is due to an immunologic response in the animals.

Although the invention has been described with reference to the above example, it will be understood that modifications and variations are encompassed within the spirit and scope of the invention. Accordingly, the invention is limited only by the following claims.

What is claimed is:

1. An isolated polynucleotide, comprising a first nucleotide sequence encoding a Her2/neu target antigen consisting of:
    a) amino acid residues 634 to 683 of SEQ ID NO: 1 operatively linked to
    b) amino acid residues 1035 to 1255 of SEQ ID NO: 1, wherein the Her2/neu target antigen consists of the amino acid sequence as set forth in SEQ ID NO: 10.

2. The polynucleotide of claim 1, wherein the first nucleotide sequence consists of the nucleotide sequence as set forth in SEQ ID NO:9.

3. The polynucleotide of claim 1, further comprising a second nucleotide sequence, which is operatively linked to the first nucleotide sequence.

4. The polynucleotide of claim 3, wherein the second nucleotide sequence comprises an expression regulatory element.

5. The polynucleotide of claim 4, wherein the expression regulatory element is a transcriptional regulatory element, a translational regulatory element, or a combination thereof.

6. The polynucleotide of claim 3, wherein the second nucleotide sequence encodes a heterologous polypeptide.

7. The polynucleotide of claim 6, which encodes a fusion protein comprising the Her2/neu target antigen and the heterologous polypeptide.

8. The polynucleotide of claim 6, wherein the polypeptide is an immunostimulatory polypeptide.

9. A isolated cell containing the polynucleotide of claim 1.

10. The cell of claim 9, which is a mammalian cell.

11. An isolated polynucleotide, comprising a first nucleotide sequence encoding a Her2/neu target antigen consisting of:
    a) amino acid residues 606 to 683 of SEQ ID NO:1 operatively linked to
    b) amino acid residues 1035 to 1255 of SEQ ID NO:1.

12. A vector, comprising the polynucleotide of claim 1 or claim 11.

13. The vector of claim 12, which is an expression vector.

14. The vector of claim 13, wherein the expression vector is a mammalian cell expression vector.

15. The vector of claim 12, which is a viral vector.

16. The vector of claim 15, wherein the viral vector is an alphavirus vector.

17. The vector of claim 16, wherein the alphavirus vector is a Venezuelan equine encephalitis virus (VEE) vector.

18. The vector of claim 15, wherein the viral vector is a retrovirus vector, an adenovirus vector, an adeno-associated virus vector, or a vaccinia virus vector.

19. The vector of claim 12, which is a plasmid vector.

20. The vector of claim 19, wherein the plasmid vector is a viral vector plasmid.

21. A isolated host cell containing the vector of claim 12.

22. An isolated polypeptide comprising a Her2/neu target antigen consisting of:
    a) amino acid residues 634 to 683 of SEQ ID NO:1 operatively linked to
    b) amino acid residues 1035 to 1255 of SEQ ID NO:1, wherein the Her2/neu target antigen consists of the amino acid sequence as set forth in SEQ ID NO:10.

23. An isolated polypeptide comprising a Her2/neu target antigen consisting of:
    a) amino acid residues 606 to 683 of SEQ ID NO:1 operatively linked to
    b) amino acid residues 1035 to 1255 of SEQ ID NO:1.

* * * * *